(12) United States Patent
De Benedictis et al.

(10) Patent No.: US 12,329,856 B2
(45) Date of Patent: Jun. 17, 2025

(54) CROSSLINKED HYALURONIC ACID COMPOSITION WITH LOCAL ANESTHETICS

(71) Applicant: BIOPOLIMERI S.R.L., San Vito Dei Normanni (IT)

(72) Inventors: Vincenzo Maria De Benedictis, San Vito Dei Normanni (IT); Piera Angela Ramires, Calimera (IT)

(73) Assignee: BIOPOLIMERI S.R.L., San Vito Dei Normanni (IT)

( * ) Notice: Subject to any disclaimer, the term of this patent is extended or adjusted under 35 U.S.C. 154(b) by 0 days.

(21) Appl. No.: 18/575,483

(22) PCT Filed: Jun. 30, 2022

(86) PCT No.: PCT/EP2022/068056
§ 371 (c)(1),
(2) Date: Dec. 29, 2023

(87) PCT Pub. No.: WO2023/275241
PCT Pub. Date: Jan. 5, 2023

(65) Prior Publication Data
US 2024/0293311 A1    Sep. 5, 2024

(30) Foreign Application Priority Data

Jul. 1, 2021 (EP) .................................. 21183109

(51) Int. Cl.
*A61K 9/06* (2006.01)
*A61K 45/06* (2006.01)
*A61K 47/10* (2017.01)
*A61K 47/36* (2006.01)

(52) U.S. Cl.
CPC ............... *A61K 9/06* (2013.01); *A61K 45/06* (2013.01); *A61K 47/10* (2013.01); *A61K 47/36* (2013.01)

(58) Field of Classification Search
CPC .......... A61K 9/06; A61K 45/06; A61K 47/10; A61K 47/36
See application file for complete search history.

(56) References Cited

U.S. PATENT DOCUMENTS

| | | | |
|---|---|---|---|
| 2004/0127698 A1* | 7/2004 | Tsai .................. | C08B 37/0072 536/53 |
| 2009/0214604 A1* | 8/2009 | Alvarez Lorenzo ... | A61K 47/40 210/600 |
| 2016/0346433 A1* | 12/2016 | Bon Betemps ........ | A61Q 19/08 |
| 2017/0020799 A1* | 1/2017 | Brillouet ............. | A61K 8/8152 |

FOREIGN PATENT DOCUMENTS

| KR | 102201482 B1 | 1/2021 |
|---|---|---|
| WO | WO 2021/064006 A1 | 4/2021 |

OTHER PUBLICATIONS

Valette et al. "Elaboration of epoxy foam by radical induced cationic frontal polymerization (RICFP): A proof of concept." Journal of Photochemistry & Photobiology, A: Chemistry, 2023, 442: 1-8. (Year: 2023).*
International Search Report and Written Opinion mailed Sep. 27, 2022 for International Application No. PCT/EP2022/068056; 17 pages.
Academic Press Dictionary of Science and Technology 1992, p. 531.
De Smedt, et al., "Viscoelastic and transient network properties of hyaluronic acid as a function of the concentration", Biorheology 1993; vol. 30, pp. 31-41.
He, et al., "Ultrasonication-assisted rapid determination of epoxide values in polymer mixtures containing epoxy resin", Anal. Methods 2014; vol. 6(12), pp. 4257-4261.
Levy, et al., "Determination of thermodynamic dissociation constants of local anaesthetic amines: influence of ionic strength" J. Pharm. Pharmacol. 1972; vol. 24, pp. 841-847.
Tetzlaff, "The pharmacology of local anesthetics", Regional Anesthesia, Anesthesiology Clinics of North America; Jun. 2000; vol. 18(2), pp. 217-233.

* cited by examiner

*Primary Examiner* — Doan T Phan
(74) *Attorney, Agent, or Firm* — Squire Patton Boggs (US) LLP

(57) ABSTRACT

The present invention refers to hyaluronic acid crosslinked with polyglycerol polyglycidyl ether containing local anesthetic agents, to a process for its preparation and its use in therapy, cosmetics and as a carrier.

9 Claims, No Drawings

CROSSLINKED HYALURONIC ACID COMPOSITION WITH LOCAL ANESTHETICS

CROSS-REFERENCE

The present application is a National Stage filing under 35 U.S.C. § 371 of International Patent Application No. PCT/EP2022/068056, filed Jun. 30, 2022, which claims the benefit of and priority to European Patent Application No. 21183109.4 filed Jul. 1, 2021, the contents of all of which are hereby incorporated by reference in their entireties for all purposes.

The present invention belongs to the field of hyaluronic acid compositions, and particularly to compositions containing hyaluronic acid crosslinked with polyglycerol polyglycidyl ether and local anesthetic agents.

BACKGROUND ART

A local anesthetic (LA) is a medication that causes absence of pain sensation in a specific location of the body without a loss of consciousness, as opposed to a general anesthetic. In particular, the LA interrupt neural conduction by inhibiting the influx (uptake) of sodium ions. In most cases, this follows their diffusion through the neural membrane into the axoplasm, where they enter sodium channels and prevent them from assuming an active or open state.

Local anesthetic agents are formed by a lipophilic group (aromatic ring), a hydrophilic group (tertiary amine) and an intermediate linkage group (ester or amide). It is known that each of these groups (components) confers distinct properties to the anesthetic molecule in terms of lipid and water solubility, which is important for having an efficient duration of action and a short onset time (i.e. time interval between the end of total local anesthetic administration and complete sensory or motor block). On one hand, it seems that the aromatic ring improves the liposolubility of the LA, which can be further enhanced by aliphatic substitutions on the amine group. Greater liposolubility enhances diffusion through nerve sheaths, as well as the neural membranes of individual axons comprising a nerve trunk. This property has been correlated with the anesthetic potency of the active ingredient because a greater bioavailable portion of an administered dose can enter neurons. Besides, on the other hand, the amine group may exist as neutral (not-ionized) tertiary amine, or as a positively charged quaternary salt (ionized). The neutral form of the local anesthetic, having the tertiary amine not ionized, is liposoluble and therefore it is the bioavailable form (and therefore, the active form). Instead, the positively charged form (having the quaternary ammonium salt) is water soluble and therefore not bioavailable (i.e. non-active). However, it seems that the positively charged form (even without being the bioavailable active form) can be actively involved in the mechanism of action of the anesthetics, allowing anesthetic cations to be more firmly attached to proteins located at receptor sites, enlarging the duration of the local anesthetic action.

Typically, local anesthetics are administered in form of a sterile injectable dosage form containing a salt of the LA (such as hydrochloride salt) and a hydrogel made of a crosslinked polysaccharide (such as hyaluronic acid). These hydrogels containing local anesthetic salts are administered through thin needles especially when they are used as fillers for aesthetic purposes or for the treatment of osteoarthritis.

Unfortunately, these injectable dosage forms have some drawbacks. On one hand, the (hydrochloride) salt of the local anesthetic contained in the hydrogel is mainly in its water soluble positively charged form (i.e. non-active form of the local anesthetic) avoiding thus the precipitation of the liposoluble form at the physiological pH of the hydrogel (i.e. the active form of the local anesthetic), increasing undesirable the onset time of the LA and compromising the efficiency of the local anesthetic by reducing the penetration capacity of the LA into the neurons. Further, on the other hand, the crosslinked hyaluronic acids (hydrogels) having a high cross-linking degree exhibit inappropriate poor flow property. In fact, the percentage of crosslinking contributes positively to the elasticity and viscosity of the hydrogel but compromises the extrudability properties through fine needles, causing pain and also inflammatory reaction as a response to the mechanical injury to the tissue (caused by the penetration of the needle during injection and by the forces that the viscoelastic hydrogel exerts on the surrounding tissues). Furthermore, (crosslinked) hyaluronic acid (HA) can also be naturally degraded in the organism by reactive oxygen species (ROS) leading to an additional transient inflammatory reaction. For all the above reasons, the crosslinked hydrogels are formulated incorporating Local Anesthetics in their composition, and most important, the Local Anesthetics should act in short time after the injection of the hydrogel.

Hence, as it is disclosed herein above, numerous factors can alter the stability of the anesthetic neutral form, contributing to the anesthetic therapeutic effect, and particularly to the onset time and the duration of the therapeutic effect. These factors can be related either to the characteristics of the local anesthetic (such as its chemical structure) or the characteristic of the hyaluronic acid hydrogel (chemical composition, degree of crosslinking and the presence of additional dissolved compounds, osmolarity and/or ionic strength), the osmolarity and/or ionic strength of the medium in which the local anesthetic is dissolved (i.e. the crosslinked hydrogel) as well as the sterilization method used for its administration.

It has been disclosed in the state of the art several strategies for the development of stable hydrogels of crosslinked hyaluronic acid hydrogels containing anesthetic agents. In particular, hydrogels of hyaluronic acid crosslinked with 1,4-butanediol diglycidyl ether (BDDE) and anesthetic agents having improved rheological properties (physical properties) have been disclosed in the state of the art. In fact, injectable aqueous compositions of hydrogel containing hyaluronic acid crosslinked with 1,4-butanediol diglycidyl ether (BDDE) and anesthetic agents and one or more polyols chosen form glycerol, sorbitol, propylene glycol, mannitol, erythritol, xylitol, maltitol and lactitol showed an improved stability to the degradation of a hyaluronic acid-based gel in vivo (enzymatic degradation by hyaluronidases, free-radical degradation, thermal degradation at 37° C.) improving the shelf-life of the hydrogel. However, all the documents are silent about the composition of the hydrogel (free polyglycerols) having the effect to increase the amount of the active form of the anesthetic inside the hydrogel in the therapeutic effect of the anesthetic agent contained in it, and even less in the effect in the release of the active ingredient (i.e. the Local Anesthetic) from it and its subsequent effect on the onset time of the anesthetic agent.

Alternatively, several strategies have been disclosed in the state of the art for increasing the efficacy and, particularly, to reduce the onset time of the local anesthetic agent. Some of them methods were based on changing the salt of the local anesthetic agent (changing hydrochloric salt for bicarbonate counter anion) and/or the use of a pH above 8. Unfortunately, these methods are poor applicable for the preparation of permanent or semi-permanent injectable medical devices containing hyaluronic acids. Other strategies were focused on the addition of substances such as surface-active agents or mannitol that increase the permeability of the LA through the lipoprotein barrier of the nerve (i.e. nerve permeation enhancers). However, side effects associate with the use of these nerve permeation enhancers has been also disclosed in the art. In particular, the main disadvantage of the use of mannitol is that mannitol is used in form of a hyperosmolar solution that can cause severe adverse effects (as edema) due to recall of water or fluids in the injection site. Therefore, the use of hyperosmolar mannitol solution is not indicated in long term applications, and not recommended (unacceptable) in form of hyperosmolar solution for osteoarticular, intradermal or intraocular applications.

Therefore, from what it is known in the art, there is still the need to provide a crosslinked hyaluronic acid having appropriate stability and rheological properties containing one or more anesthetic agents with improved bioavailability; particularly with enhanced therapeutic effect caused by the reduced onset time.

SUMMARY OF INVENTION

The inventors of the present invention have surprisingly provided a safety and stable crosslinked hyaluronic acid local anesthetic containing composition that allows enhancing the release of the active form of the local anesthetic contained in it, resulting in a fast therapeutic effect (reduction of the onset time of action). In opposition to the state of the art, in which the non-active form of Local Anesthetic is mainly released from the hydrogel. In particular, the crosslinked hyaluronic acid composition comprising a specific concentration of free polyglycerols and a PPE crosslinked hyaluronic acid having appropriate mechanical properties, low enzymatic/oxidative degradation rate, and adequate biocompatibility for being used in in vivo applications without causing the undesirable side effects associate to its administration, particularly to its injectable application. In particular, the inventors have found that the combination of a hyaluronic acid crosslinked with polyglycerol diglycidyl ether (PPE), and the specific concentration of free polyglycerols disclosed in the present invention allows reducing the pain and inflammatory undesirable side effects associated with the administration of HA's compositions, because a reduction of the onset of the anesthetic agent is achieved. This short onset is associated with the fastest action of the local anesthetics, caused by an increased bioavailability of the local anesthetic active form but without compromising the mechanical properties of the hyaluronic acid.

Without being bound to any theory, the inventors attribute the increased bioavailability of the local anesthetic (increasing the percentage of the active form of the local anesthetic) to a combination of the controlled concentration of the free polyglycerols, their molecular weight along with the structure of the crosslinker PPE which also positively affect the kinetic release of the local anesthetic from the hydrogel to the surrounding tissues. In addition, the mechanical properties and the degradation resistance of the PPE cross-linked hyaluronic acid to a combination effect of the structure of the crosslinker along with its cohesive properties derived from the (covalent and non-covalent) interactions between the HA and the PPE. In particular, the interaction of the PPE with the HA creates a dense three-dimensional HA network that holds the hydrogel matrix intact and limits the enzyme's ability to infiltrate the implant and degrade the 3D-network even at low cross-linking degree.

As it is demonstrated in the experimental section, the composition of the present invention allows having inside the 3D-HA network a pKa value of the local anesthetic closer to the physiological pH, resulting in having inside the 3D-HA network a higher concentration of the active form (i.e. the liposoluble form at the physiological pH) of the local anesthetic than the theoretical concentration predicted by the Henderson-Hasselbalch equation at a given physiologically acceptable pH. This increased amount of the active form of the local anesthetic inside results in turn in the reduction of the onset time. In fact, it is shown that the experimentally pKa value of the local anesthetic located inside the 3D-HA composition of the present invention is lower than the theoretically pKa value.

Furthermore, the inventors have also demonstrated a strong correlation between this in vivo rapid onset and efficacy of the anesthetics disclosed in the present invention, with 3D-HA network, along with the presence of a specific concentration of free polyglycerols.

Without being bound to any theory, it seems that the composition of the invention and particularly the synergic effect of the combination of the PPE crosslinker and the free polyglycerols confers the change in the bioavailability of the Local Anesthetic inside the hydrogel and the rapid diffusion of the drug from it.

In particular, it appears that the amphiphilic character of the PPE used as crosslinker, its molecular weight and the crosslinking degree, in combination with the amphiphilic character of free polyglycerols deriving from the hydrolytic epoxy ring opening of unreacted PPE crosslinker as well as from the natural hydrolysis of the hyaluronic acid chain bonded crosslinker, confers an unexpected stabilization of the active form of the anesthetic inside the matrix. This causes a quantitative increment in the percentage of the bioavailable form (form B) of the anesthetic agent in comparison to the percentage predicted by thermodynamic equation and found in products known in the state of the art (i.e. the thermodynamic pKa value is decreased from 2.5% to 10% of its predicted value); at the same time, the three-dimensional structure of the crosslinked HA contributes to a fastest kinetic release of the anesthetic agent from the 3D-crosslinked matrix of the HA, resulting in a rapid diffusion of the active form of the drug (shortening its onset).

Finally, the composition of the invention comprising the PPE crosslinked HA, the specific concentration of free polyglycerols and the anesthetic agents exhibits good flow properties. Besides, as it is mentioned above, the injection of the composition of the present invention renders low or no inflammation and pain perception by the patients during and after its application.

To sum up, the composition of the present invention has (a) such amphiphilic character of the hyperbranched PPE crosslinker, (b) such specific concentration of free hyperbranched polyols fragments, and (c) such molecular weight of the free hyperbranched polyols that the combination of them allow increasing the liposoluble active form of the local anesthetic inside the composition (i.e. having a form of the local anesthetic higher than the molar concentration expected according to the Handerson-Hasselbach equation). In turn, the crosslinked 3D matrix of the hydrogel composition of the present invention (i.e. physical property) provides a faster kinetic release of a higher amount of the liposoluble active form of the local anesthetic; resulting in a fast onset of the local anesthetic. Thus, the first aspect of the invention relates to a composition comprising:

A) one or more crosslinked hyaluronic acids selected from the group consisting of one or more of crosslinked hyaluronic acids of formula (I);

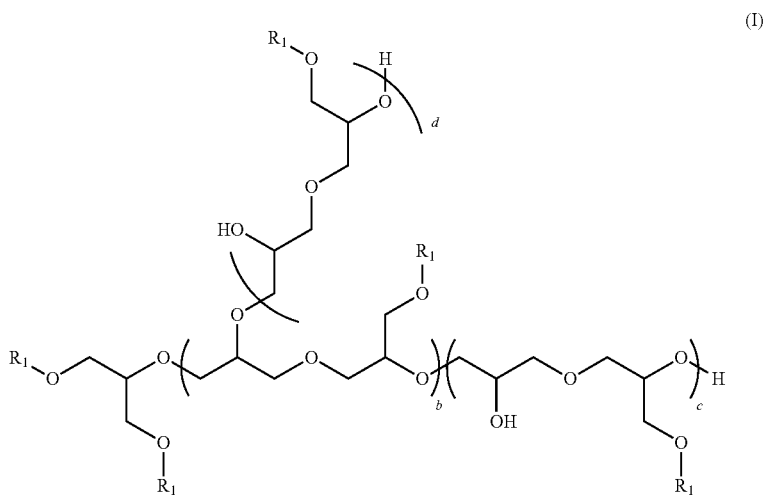

one or more of crosslinked hyaluronic acids of formula (II);

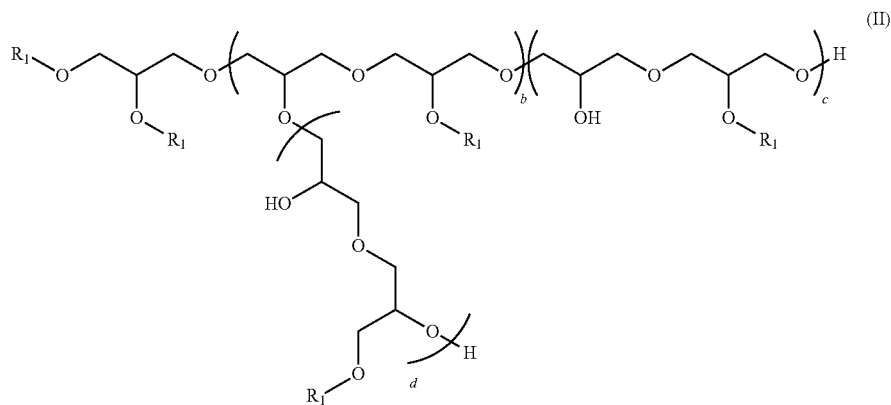

and a mixture of one or more crosslinked hyaluronic acids of formula (I) and one or more of crosslinked hyaluronic acids of formula (II);

B) one or more polyglycerols selected from the group consisting of one or more polyglycerols of formula (III);

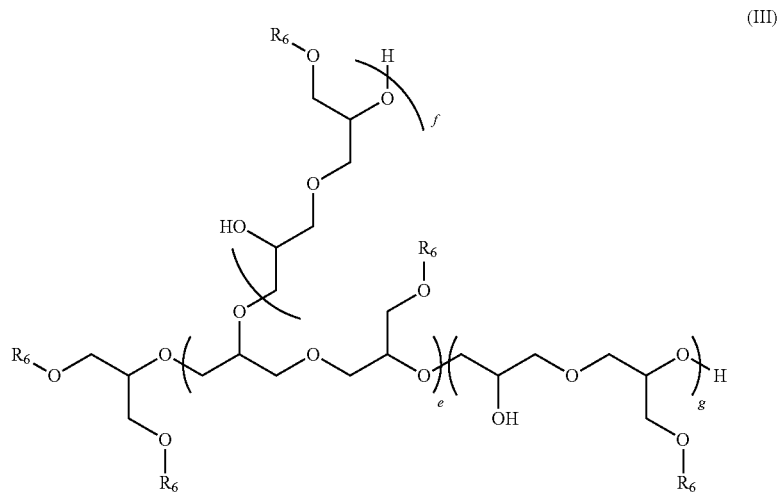

(III)

one or more polyglycerols of formula (IV);

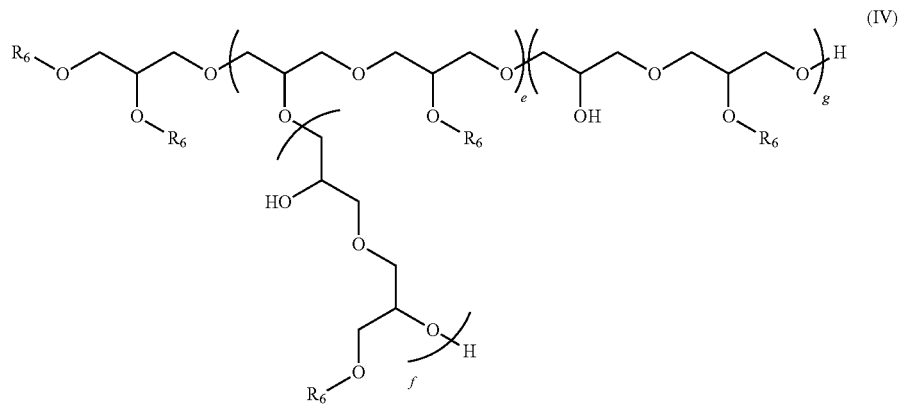

(IV)

and a mixture of one or more polyglycerols of formula (III) and one or more polyglycerols of formula (IV);

C) one or more local anesthetic agents or a salt thereof; and

D) optionally, one or more acceptable excipients or carriers;

wherein:

each $R_1$ is independently selected from the group consisting of $R_2$, $R_3$, $R_4$ and $R_5$;

$R_2$

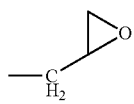

$R_3$ is

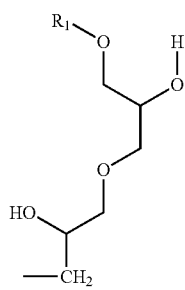

$R_4$ is

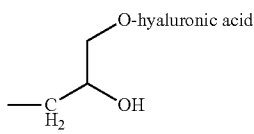

$R_5$ is

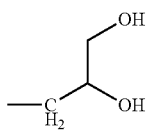

each $R_6$ is independently selected from the group consisting of $R_3$ and $R_5$; b is an integer selected from the group consisting of 1 to 70; c is an integer selected from the group consisting of 0 to 70; d is an integer selected from the group consisting of 0 to 70; e is an integer selected from the group consisting of 1 to 50; f is an integer selected from the group consisting of 0 to 50; g is an integer selected from the group consisting of 0 to 50; the crosslinked hyaluronic acids of formula (I) or formula (II) have a crosslinking percentage from 0.030 to 0.900%; and the polyglycerols of formula (III) or formula (IV) have a weight average molecular weight ($M_w$) from 240 to 3.700 Da measured by size exclusion chromatography coupled with UV-visible and Mass detector (SEC/UV/MS); with the proviso that: in the crosslinked hyaluronic acids of formula (I) or formula (II) at least one $R_1$ is $R_4$; and in the polyglycerols of formula (III) or formula (IV), if R1 is present, then $R_1$ is other than $R_4$.

The second aspect of the invention relates to a process for the preparation of the first aspect of the invention.

The third aspect of the invention relates to the composition of the first aspect of the invention for use in therapy.

The fourth aspect of the invention relates to the use of the composition of the first aspect of the invention in cosmetic; particularly as dermal filler.

And the fifth aspect of the invention relates to the use of the composition of the first aspect of the invention as carrier; particularly as drug-delivery system.

DETAILED DESCRIPTION OF THE INVENTION

All terms as used herein in this application, unless otherwise stated, shall be understood in their ordinary meaning as known in the art. Other more specific definitions terms as used in the present application are as set forth below and are intended to apply uniformly throughout the specification and claims unless an otherwise expressly set out definition provides a broader definition.

For the purposes of the present invention, any ranges given include both the lower and the upper endpoints of the range. Ranges given, such as temperatures, times, weights, and the like, should be considered approximate, unless specifically stated. The term "about" or "around" as used herein refers to a range of values ±10% of a specified value. For example, the expression "about 0.5" or "around 0.5" includes ±10% of 0.5, i.e. from 0.45 to 0.55.

The term "percentage (%) by weight" refers to the percentage of each ingredient in relation to the total weight of the composition.

As it is disclosed above, the first aspect of the present invention refers to a composition comprising: a) one or more crosslinked hyaluronic acids selected from the group consisting of one or more of crosslinked hyaluronic acids of formula (I); one or more of crosslinked hyaluronic acids of formula (II); and a mixture of one or more crosslinked hyaluronic acids of formula (I) and one or more of crosslinked hyaluronic acids of formula (II). In an embodiment, the composition of the first aspect of the invention comprises: a) one or more crosslinked hyaluronic acids of formula (I). In an embodiment, the composition of the first aspect of the invention comprises: a) one or more crosslinked hyaluronic acids of formula (II). In an embodiment, the composition of the first aspect of the invention comprises: a) a mixture of one or more crosslinked hyaluronic acids of formula (I) and one or more of crosslinked hyaluronic acids of formula (II).

For the purpose of the invention the term "hyaluronic acid", "hyaluronan", and the abbreviature "HA" have the same meaning and are used interchangeable. They refer to an anionic non-sulphated glycosaminoglycan (GAG) having a linear high molecular weight polysaccharide that consists of repeating monomers of D-glucuronic acid and N-acetyl-D-glucosamine, linked via alternating β-(1→4) and β-(1→3) glycosidic bonds. Its chemical structure corresponds to the following formula:

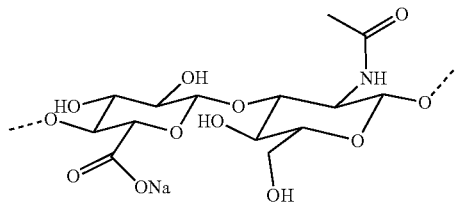

For the purpose of the present invention the term "hyaluronic acid" also encompasses its physiological acceptable salt such as pharmaceutically or cosmetically acceptable salt of hyaluronic acid. In an embodiment, the crosslinked polysaccharide of the present invention is one wherein the polysaccharide is a pharmaceutically or cosmetically acceptable salt of hyaluronic acid. There is no limitation on the type of hyaluronic acid salt that can be used, as long as they are pharmaceutically or cosmetically acceptable when used for therapeutic or cosmetic purposes. Hyaluronic acid and a salt thereof may differ in some physical properties, but they are equivalent for the purposes of the present invention and the skin-friendly properties of hyaluronic acid are extensible to a pharmaceutically or cosmetically acceptable salt, in particular to its sodium salt (or sodium hyaluronate) and potassium salt (potassium hyaluronate). The term "physiologically acceptable salt" refers to a salt physiologically tolerated by the patient (such as mammals including humans being). Particularly, the term "pharmaceutically acceptable salt" refers to the salt appropriate for use in pharmaceutical technology for the preparation of compositions for medical use and, the term "cosmetically acceptable salt" or "dermatologically acceptable salt" used interchangeably in this document refers to the salt appropriate for use in human skin contact without toxicity, incompatibility, instability, inappropriate allergic response, among others. In particular, the term "pharmaceutical or cosmetically acceptable salt" covers commonly used salts such as e.g. alkaline metal salts. The preparation of pharmaceutically acceptable salts of hyaluronic acid can be carried out by methods known in the technique. Non-limiting examples of pharmaceutical or cosmetically acceptable salts of hyaluronic acid appropriate for the present invention include inorganic salts such as sodium hyaluronate, magnesium hyaluronate, potassium hyaluronate, zinc hyaluronate and cobalt hyaluronate, as well as organic salts such as tetrabutylammonium hyaluronate. In an embodiment, the pharmaceutically or cosmetically acceptable salt of hyaluronic acid is a salt of a selected alkaline metal of sodium salt (CAS No: 9067-32-7) or potassium salt (CAS No: 31799-91-4).

In an embodiment, the composition of the invention is one wherein the concentration of the hyaluronic acid in the crosslinked hyaluronic acid of formula (I) or formula (II) is from 1 to 50 mg/ml; particularly from 10 to 30 mg/ml. For the purpose of the present invention, as the density of the solutions is close to 1 (1 mL=1 g), therefore, the concentration expressed as mg/mL is interchangeably with mg/g. The concentration of the hyaluronic acid can be measured by any appropriate method disclosed in the state of the art. In the present invention the concentration of the hyaluronic acid is measured by gravimetric measurement of dry residue obtained after dehydration of the hydrogel in ventilated oven at 105° C. for a suitable time.

In an embodiment, the composition of the invention is one wherein the molecular weight of the hyaluronic acid of the crosslinked hyaluronic acid of formula (I) or formula (II) is from 100 to 3000 kDa measured by size exclusion chromatography (SEC); particularly from 250 to 2000 kDa.

The hyaluronic acid of the present invention is a "crosslinked" hyaluronic acid. The term "crosslinked" refers to a hyaluronic acid that have three-dimensional crosslink network wherein the network is formed by a starting hyaluronic acid that has been collapsed by one or more crosslinking agents. The term "crosslinking" refers in the polymer science field to the use of cross-links to promote a difference in the physical properties of the polymers (hyaluronic acid). The term "crosslink" refers to bonds that is formed by the aperture of the epoxide ring of the crosslinking agent of the present invention by the hydroxyl group of the hyaluronic acid. The term "crosslinker" or "crosslinking agent" which is herein used interchangeably refers to a compound having the ability to cross-link one or more hyaluronic acid chains.

The terms "crosslinking percentage", "percentage (%) of crosslinking", "cross-linking degree" and the abbreviation "C.D." have the same meaning and they are used interchangeable. They refer to the ratio between the crosslinked modified hyaluronic acid monomeric units and the unmodified hyaluronic acid monomeric units expressed in percentage. Commonly, the measurement of the cross-linking degree (C.D.) of materials could be evaluated using different methods well known in the state of the art. Some methods are direct, such as $^1$H NMR or quantitative GPC analysis of polymer's fragments after enzymatic digestion. Other methods are indirect, by rheological measurements, by compression or by oscillatory tests. Normally all these methods are comparative and allow to distinguish different cross-linking degree inside the same polymer's family. In the present invention, the cross-linking degree value is mathematically calculated from the value of G' obtained by rheological measurements using the following equation 1:

$$C.D.(\%) = \frac{100 * MW_{rep \cdot unit}}{M_e} \quad \text{(Eq. 1)}$$

wherein:

$MW_{rep, unit}$ is 401 Da which is the molecular weight of the hyaluronic monomeric repeating unit, $M_e$ is mathematically calculated using the inverse formula of the following equation 2:

$$G' \cong \frac{R \cdot T \cdot c}{M_e}\left(1 - 2\frac{M_e}{M_n}\right) \quad \text{(Eq. 2)}$$

wherein:

G' is experimentally obtained by rheological measurements using rotational rheometer, R·T is the thermal energy, c is the hyaluronic acid concentration, $M_n$ is the number average molecular mass of the hyaluronic acid (see. S. C. De Smedt, et al. "Viscoelastic and transient network properties of hyaluronic acid as a function of the concentration," Biorheology, 1993. vol. 30(1), pp. 31-41).

In an embodiment, the composition of the first aspect of the invention comprises: A) one or more crosslinked hyaluronic acids of formula (I), or alternatively of formula (II) have a crosslinking percentage from 0.03% to 0.9%; particularly from 0.045 to 0.077%. For the purpose of the present application, the crosslinking percentage is measured from the value of G' obtained by rheological measurements using the equation 1 as defined above.

In an embodiment, the composition of the first aspect of the invention comprises: a) a mixture of one or more crosslinked hyaluronic acids of formula (I) and one or more of crosslinked hyaluronic acids of formula (II). All the embodiments mentioned above for the compositions comprising one or more crosslinked hyaluronic acids of formula (I) or alternatively of formula (II), also apply for the composition comprising a mixture of one or more crosslinked hyaluronic acids of formula (I) and one or more of crosslinked hyaluronic acids of formula (II).

In an embodiment, the composition of the first aspect of the invention comprises: a) one or more crosslinked hyaluronic acids selected from the group consisting of one or more crosslinked hyaluronic acids of formula (I); one or more of crosslinked hyaluronic acids of formula (II); and a mixture of one or more crosslinked hyaluronic acids of formula (I) and one or more of crosslinked hyaluronic acids of formula (II); wherein the one or more crosslinked hyaluronic acids of formula (I) or of formula (II) are obtainable by using one or more polyglycerol diglycidyl ether (PPE) crosslinking agents.

In an embodiment, the composition of the first aspect of the invention comprises: a) one or more crosslinked hyaluronic acids of formula (I), or alternatively of formula (II) obtained by using the crosslinker PPE having an average EEW from 100 to 7.000 g/eq; particularly from 100 to 600 g/eq measured by ultrasonication-assisted rapid titration with HCl. The term "epoxy equivalent weight", "average EEW" and the abbreviation "EEW" have the same meaning and they are used interchangeable. The EEW is the weight of crosslinking agent, in grams, which contains one gram-equivalent of epoxy. EEW refers to the content of epoxy groups present in one gram of the crosslinking agents disclosed in the present invention and expressed in g/eq. The EEW was experimentally measured using the quantitative ultrasonication-assisted titration with HCl for the rapid determination of epoxides disclosed in the state of the art (cf. He, Z., et al., "Ultrasonication-assisted rapid determination of epoxide values in polymer mixtures containing epoxy resin". Analytical Methods, 2014, vol. 6(12), pp. 4257-4261).

In an embodiment, the composition of the first aspect of the invention comprises: a) one or more crosslinked hyaluronic acids of formula (I), or alternatively of formula (II) obtained by using the crosslinker PPE having a Mw from 204 to 15.000 Da, particularly from 204 to 3.500 Da, measured by size exclusion chromatography (SEC). The terms "molecular weight", "weight average molecular weight", "weight-average molar mass", "mass average molar mass", "average Mw" and the abbreviation "$M_W$" have the same meaning and they are used interchangeable. The mass average molar mass is calculated by the following equation:

$$\overline{M}_w = \frac{\sum_i N_i M_i^2}{\sum_i N_i M_i}$$

where $N_i$ is the number of molecules of molecular mass $M_i$. The mass average molecular mass can be determined by static light scattering, small angle neutron scattering, X-ray scattering, and sedimentation velocity. In the present application the Mw is determinate by size exclusion chromatography (SEC).

In an embodiment, the composition of the first aspect of the invention comprises: a) one or more crosslinked hyaluronic acids selected from the group consisting of one or more crosslinked hyaluronic acids of formula (I); one or more of crosslinked hyaluronic acids of formula (II); and a mixture of one or more crosslinked hyaluronic acids of formula (I) and one or more of crosslinked hyaluronic acids of formula (II); wherein the one or more crosslinked hyaluronic acids of formula (I) or of formula (II) are obtainable by using as a crosslinker a polyglycerol diglycidyl ether (PPE) having a Mw from 204 to 15.000 g/mole; and EEW from 100 to 7.000 g/eq. In an embodiment, the composition of the first aspect of the invention comprises: a) one or more crosslinked hyaluronic acids selected from the group consisting of one or more crosslinked hyaluronic acids of formula (I); one or more of crosslinked hyaluronic acids of formula (II); and a mixture of one or more crosslinked hyaluronic acids of formula (I) and one or more of crosslinked hyaluronic acids of formula (II); wherein the one or more crosslinked hyaluronic acids of formula (I) or of formula (II) are obtainable by using as a crosslinker a polyglycerol diglycidyl ether (PPE) having a Mw from 204 to 3.500 g/mole; and EEW from 100 to 600 g/eq.

In an embodiment, the composition of the first aspect of the invention comprises: a) one or more crosslinked hyaluronic acids of formula (I), or alternatively of formula (II) have a crosslinking percentage from 0.03% to 0.9%; and obtained by using the crosslinker PPE having a Mw from 204 to 15.000 g/mole; and EEW from 100 to 7.000 g/eq.

In an embodiment, the composition of the first aspect of the invention comprises: a) one or more crosslinked hyaluronic acids of formula (I), or alternatively of formula (II) have a crosslinking percentage from 0.045% to 0.077%; and obtained by using the crosslinker PPE having a Mw from 204 to 3.500 g/mole; and EEW from 100 to 600 g/eq.

In an embodiment, the composition of the first aspect of the invention comprises: a) one or more crosslinked hyaluronic acids selected from the group consisting of one or more crosslinked hyaluronic acids of formula (I); one or more of crosslinked hyaluronic acids of formula (II); and a mixture of one or more crosslinked hyaluronic acids of formula (I) and one or more of crosslinked hyaluronic acids of formula (II); wherein the amount of $R_2$ is lower than 2 ppm on the total weight of the crosslinked hyaluronic acid of formula (I) and of formula (II). The amount of $R_2$ is experimentally measured using the quantitative ultrasonication-assisted titration with HCl for the rapid determination of epoxides disclosed in He, Z., et al., "Ultrasonication-assisted rapid determination of epoxide values in polymer mixtures containing epoxy resin". Analytical Methods, 2014, vol. 6(12), pp. 4257-4261.

As it is disclosed above, the first aspect of the present invention refers to a composition comprising: B) one or more polyglycerols selected from the group consisting of one or more polyglycerols of formula (III); one or more polyglycerols of formula (IV); and a mixture of one or more polyglycerols of formula (III) and one or more polyglycerols of formula (IV). In an embodiment, the composition of the first aspect of the invention comprises: B) one or more polyglycerols of formula (III). In an embodiment, the composition of the first aspect of the invention comprises: B) one or more polyglycerols of formula (IV).

For the purpose of the present invention the polyglycerols of formula (III) or the polyglycerols of formula (IV) can also name as "free" polyglycerols of formula (III) or "free" polyglycerols of formula (IV), respectively.

In an embodiment, the composition of the first aspect of the invention comprises: B) one or more polyglycerols of formula (III) or formula (IV) are obtainable by using one or more polyglycerol diglycidyl ether (PPE) crosslinking agents having a weight average molecular weight ($M_w$) from 240 to 3.700 Da measured by size exclusion chromatography coupled with UV-visible and Mass detector (SEC/UV/MS); particularly from 314 to 1129 Da.

In an embodiment, the composition of the invention is one having a concentration of polyglycerols of formula (III) or of formula (IV) in the composition from 0.45 to 25 mg/ml; particularly from 2 to 20 mg/mL. The concentration of the polyglycerols of formula (III) or of formula (IV) can be measured by any appropriate method disclosed in the state of the art. In the present invention the concentration of the polyglycerols of formula (III) or of formula (IV) is measured by size exclusion chromatography coupled with UV-visible and Mass detector (SEC/UV/MS).

In an embodiment, the composition of the invention is one wherein the one or more polyglycerols of formula (III) or formula (IV) are selected from the group consisting of:

a compound of formula (1);

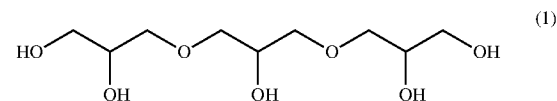 [SMILES: OCC(O)COCC(O)COCC(O)CO]

(1)

a compound of formula (2);
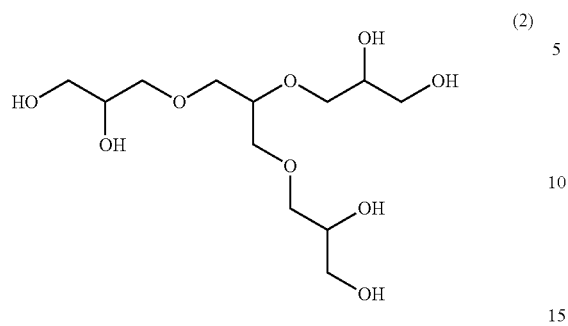
a compound of formula (3);
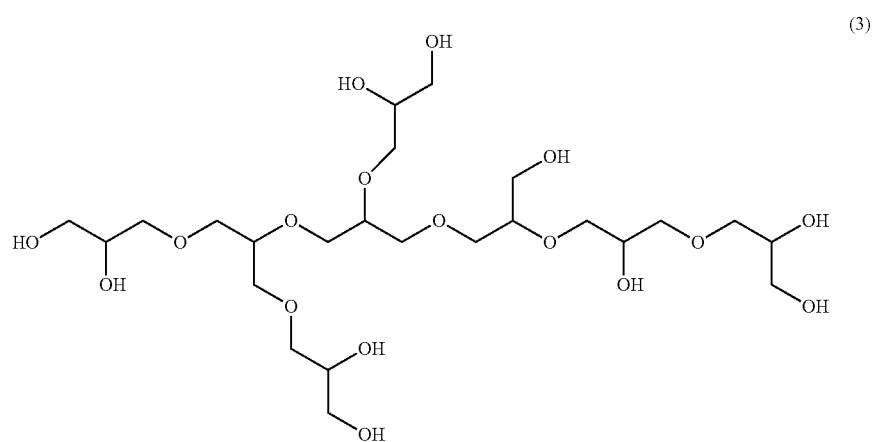 [SMILES: OCC(O)COCC(O)COC(CO)COCC(COC(COCC(O)CO)COCC(O)CO)OCC(O)CO]
a compound of formula (4);
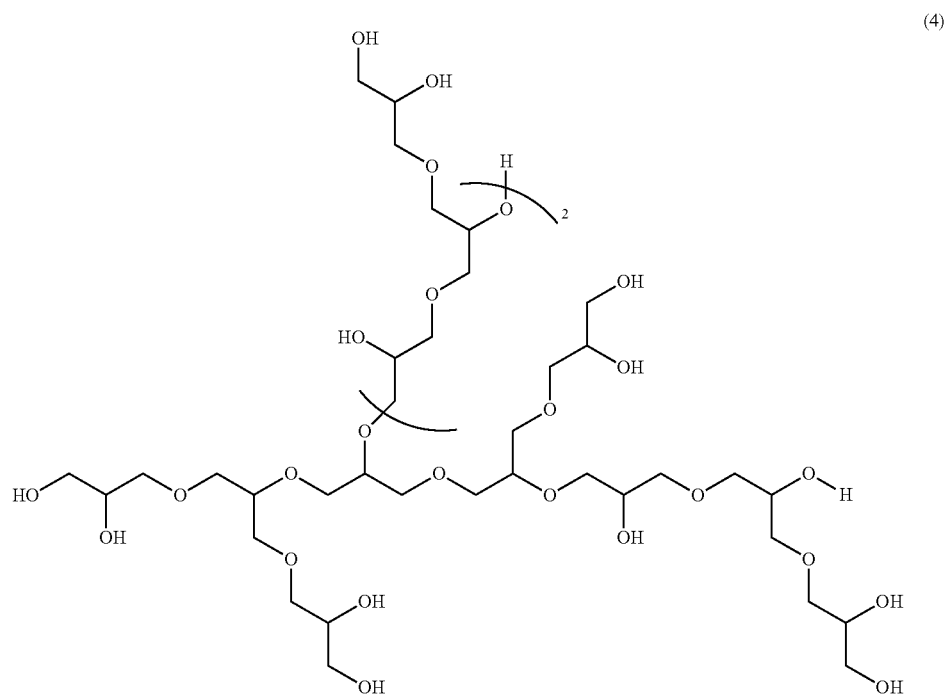

a compound of formula (5);

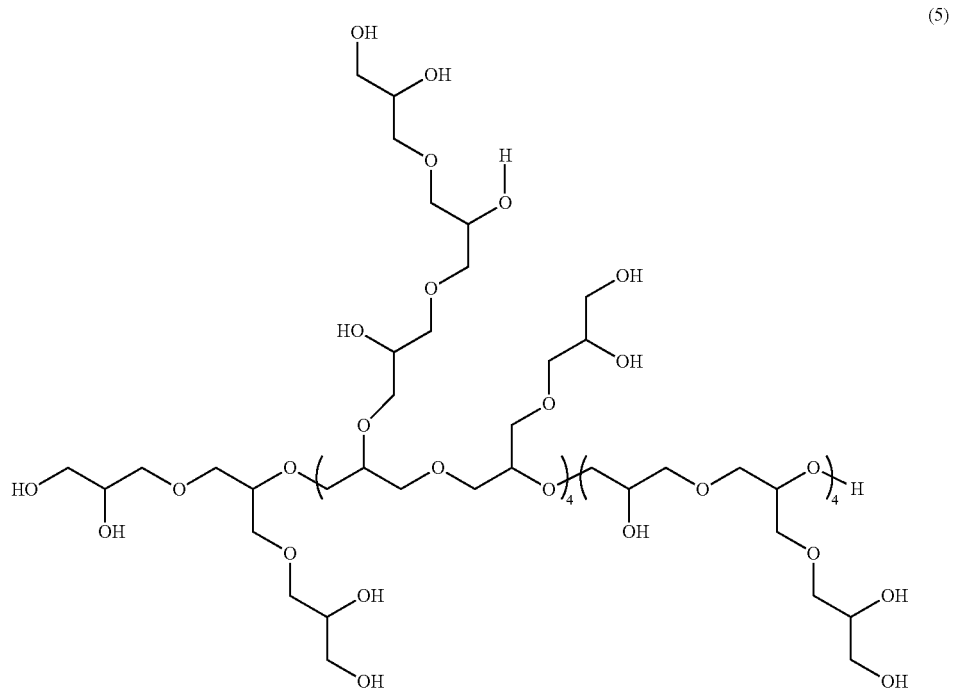

a compound of formula (6);

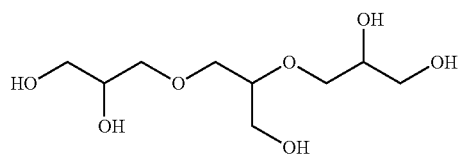

and a mixture thereof.

In an embodiment, the composition of the first aspect of the invention comprises: B) a mixture of one or more polyglycerols of formula (III) and one or more polyglycerols of formula (IV). All the embodiments mentioned above for the compositions comprising B) one or more polyglycerols of formula (III) or alternatively one or more polyglycerols of formula (IV) also apply for the composition comprising a mixture of one or more polyglycerols of formula (III) and one or more polyglycerols of formula (IV).

As it is disclosed above, the first aspect of the present invention refers to a composition comprising: C) an effective amount of one or more local anesthetic agents or a salt thereof. The term "anesthetic" refers to an agent that causes loss of sensation in a human or other mammal with or without the loss of consciousness. More particularly, the term "local anesthetic" refers to an anesthetic agent that induces local anaesthesia by reversibly inhibiting peripheral nerve excitation and/or conduction. As used herein, the term "effective amount" refers to an amount of one or more local anesthetic agent that produces the above-mentioned anesthetic effect, e.g., a partial or total loss of sensation, inhibition of sensory perception, or inhibition of motor function.

Local anesthetics suitable for use in the present invention include, but are not limited to, those anesthetic agents or salts thereof comprising at least one lipophilic moiety and a hydrophilic moiety selected from the group consisting of ambucaine, amolanone, amylocaine, articaine, benoxinate, benzocaine, betoxycaine, biphenamine, bupivacaine, butacaine, butamben, butanilicaine, butethamine, butoxycaine, chloroprocaine, cocaethylene, cocaine, cyclomethycaine, dibucaine, dimethisoquin, dimethocaine, diperodon, dicyclomine, ecgonidine, ecgonine, etidocaine, beta-eucaine, euprocin, fenalcomine, farmocaine, fomocaine, hexylcaine, hydroxytetracaine, isobutyl p-aminobenzoate, leucinocaine mesylate, levoxadrol, lidocaine, mepivacaine, meprylcaine, metabutoxycaine, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and a mixture thereof.

In an embodiment, the composition of the invention is one wherein the local anesthetic agents or a salt thereof is selected from the group consisting of amide-based local anesthetics such as lidocaine, mepivacaine, articaine or a mixture thereof. In an embodiment, the composition of the invention is one wherein the local anesthetic agents or a salt thereof is lidocaine or a salt thereof. In an embodiment, the composition of the invention is one wherein the local anesthetic agents or a salt thereof is mepivacaine or a salt thereof. In an embodiment, the composition of the invention is one wherein the local anesthetic agents or a salt thereof is articaine or a salt thereof.

The salts of local anesthetic encompasses salts formed from acceptable non-toxic acids including inorganic or organic acids. There is no limitation regarding the salts, except that they must be therapeutically or cosmetic acceptable when they are used for pharmaceutical or cosmetic purposes, respectively. Most of the acceptable salts are commercially available. If not, these salts can be prepared following the processes disclosed in the state of the art, which involves starting from acceptable non-toxic acids, including inorganic and organic acids. Such acids include for instance acetic, benzenesulfonic, benzoic, camphor sulfonic, citric, ethansulfonic, fumaric, gluconic, glutamic, hydrobromic, hydrochloric, lactic, maleic, malic, mandelic, methanesulfonic, phosphoric, succinic, sulfuric, tartaric, p-toluensulfonic acid and hydrochloride. For instance, they can be prepared from the parent compound, which contains a basic moiety, by conventional chemical methods. Generally, such salts are, for example, prepared by reacting the free base form of this compound with a stoichiometric amount of the appropriate acceptable acid in water or in an organic solvent or in a mixture of them. For the purpose of the present invention, the term "pharmaceutically acceptable salts" used herein encompasses any salt formed from pharmaceutically acceptable non-toxic acids as defined above. The term "cosmetic acceptable salts" used herein encompasses any salt formed from cosmetic acceptable non-toxic acids as defined above.

In an embodiment, the composition of the invention is one wherein the local anesthetic agents is in form of a salt. In an embodiment, the composition of the invention comprises lidocaine hydrochloride salt. In an embodiment, the composition of the invention comprises mepivacaine hydrochloride salt. In an embodiment, the composition of the invention comprises articaine hydrochloride salt.

In an embodiment, the composition of the present invention comprises: C) an effective amount of one or more local anesthetic agents or a salt thereof, having an experimental pKa value calculated by the Henderson-Hasselbalch equation that is from 2.5 to 10% less than the predicted thermodynamic pKa value calculated by the Henderson-Hasselbalch equation.

For the purpose of the invention, the term "thermodynamic pKa value" (abbreviated as pKaT) is the pKa value tabulated in the state of the art (cf. cf. René. Levy et al. "Determination of thermodynamic dissociation constants of local anaesthetic amines: influence of ionic strength" J. Pharm. Pharmac., 1972, vol. 24, pp. 841-847), and calculated from the dissociation equilibrium constant of a weak acid in absence of perturbating equilibrium agents (cf. René. Levy et al.).

The term "experimental pKa value" (abbreviated as pKaS) is the pKa experimentally calculated, using the Henderson-Hasselbalch equation, starting from pH, [B] and [BH+] values measured experimentally using respectively pHmeter and by size exclusion chromatography coupled with UV-visible and Mass detector (SEC/UV/MS) in presence of perturbating equilibrium agents (i.e. free polyglycerols and PPE crosslinked hyaluronic acid).

For the purpose of the invention, the Henderson-Hasselbalch equation reads as follows:

$$\text{pH} = pKa + \log\frac{[B]}{[BH^+]}$$

wherein:
pH is the $-\log([H^+])$,
pKa is the $-\log$ of the dissociation equilibrium constant of the weak acid;
[B] ([base]) is the concentration of the conjugate basic form of the Local Anesthetic; and
[BH+] ([acid]) is the conjugate acidic form of the local anesthetic.

Deriving the values of [B] and [BH+] from the following equilibrium:

$$BH^+ \underset{}{\overset{Ka}{\rightleftharpoons}} B + H^+$$

The value of the pKa corresponds to the thermodynamic pKa value for each local anesthetic tabulated in the state of the art as defined above (cf. René. Levy et al. "Determination of thermodynamic dissociation constants of local anaesthetic amines: influence of ionic strength" J. Pharm. Pharmac., 1972, vol. 24, pp. 841-847).

In an embodiment, the composition of the present invention comprises: C) an effective amount of lidocaine or a salt thereof as one or more local anesthetic agents and having an experimental pKa value from 7.2 to 7.8 calculated by the Henderson-Hasselbalch equation. In an embodiment, the composition of the present invention comprises: C) an effective amount of mepivacaine or a salt thereof as one or more local anesthetic agents and having an experimental pKa value from 7.1 to 7.7 calculated by the Henderson-Hasselbalch equation. In an embodiment, the composition of the present invention comprises: C) an effective amount of articaine or a salt thereof as one or more local anesthetic agents and having an experimental pKa value from 7.0 to 7.5 calculated by the Henderson-Hasselbalch equation.

In an embodiment, the composition of the present invention comprises: C) an effective amount of one or more local anesthetic agents or a salt thereof, having a percentage of neutral form B of the local anesthetic determined by GC/MS that is from 40% to 160% higher than the predicted value calculated by the Henderson-Hasselbalch equation as disclosed in the present invention.

In an embodiment, the composition of the present invention comprises: C) an effective amount of lidocaine or a salt thereof as one or more local anesthetic agents and having from 25% to 63% of the percentage of neutral form B of lidocaine or a salt thereof determined by GC/MS at about pH 7.4. In an embodiment, the composition of the present invention comprises: C) an effective amount of lidocaine or a salt thereof as one or more local anesthetic agents and having from 17% to 34% of the percentage of neutral form B of lidocaine or a salt thereof determined by GC/MS at about pH 7.2. In an embodiment, the composition of the present invention comprises: C) an effective amount of lidocaine or a salt thereof as one or more local anesthetic agents and having from 12% to 25% of the percentage of neutral form B of lidocaine or a salt thereof determined by GC/MS at about pH 7.0.

In an embodiment, the composition of the present invention comprises: C) an effective amount of mepivacaine or a salt thereof as one or more local anesthetic agents and having from 29% to 65% of the percentage of neutral form B of mepivacaine or a salt thereof determined by GC/MS at about pH 7.4. In an embodiment, the composition of the present invention comprises: C) an effective amount of mepivacaine or a salt thereof as one or more local anesthetic agents and having from 21% to 40% of the percentage of neutral form B of mepivacaine or a salt thereof determined by GC/MS at about pH 7.2. In an embodiment, the composition of the present invention comprises: C) an effective amount of mepivacaine or a salt thereof as one or more local anesthetic agents and having from 15% to 26% of the percentage of neutral form B of mepivacaine or a salt thereof determined by GC/MS at about pH 7.0.

In an embodiment, the composition of the present invention comprises: C) an effective amount of articaine or a salt thereof as one or more local anesthetic agents and having from 41% to 70% of the percentage of neutral form B of articaine or a salt thereof determined by GC/MS at about pH 7.4. In an embodiment, the composition of the present invention comprises: C) an effective amount of articaine or a salt thereof as one or more local anesthetic agents and having from 29% to 50% of the percentage of neutral form B of articaine or a salt thereof determined by GC/MS at about pH 7.2. In an embodiment, the composition of the present invention comprises: C) an effective amount of articaine or a salt thereof as one or more local anesthetic agents and having from 21% to 40% of the percentage of neutral form B of articaine or a salt thereof determined by GC/MS at about pH 7.0.

As it is mentioned above, the composition of the present invention optionally comprises D) one or more acceptable excipients or carriers. In an embodiment, the composition comprises: D) one or more acceptable excipients or carriers. The appropriate excipients and/or carriers, their amounts as well as the experimental process conditions for their preparation, can readily be determined by those skilled in the art according to the field and the type of formulation being prepared.

In an embodiment, the composition of the invention is a "pharmaceutical composition" which comprises: a therapeutically effective amount of the one or more crosslinked hyaluronic acids of formula (I), of formula (II) or a mixture thereof; a therapeutically effective amount of the one or more polyglycerols of formula (III) or formula (IV) or a mixture thereof; a therapeutically effective amount of one or more anesthetic agents, and optionally, one or more pharmaceutically acceptable excipients or carriers. The term "pharmaceutical composition" refers to a composition suitable for use in the pharmaceutical technology with medical use. The term "therapeutically effective amount" as used herein, refers to the amount of a crosslinked hyaluronic acids, polyglycerols, and anesthetic agents that, when administered, is sufficient to prevent development of, or treat, cure, or alleviate to some extent, one or more of the symptoms of the disease which is addressed. The dose of the therapeutically effective amount of crosslinked hyaluronic acids, polyglycerols, and anesthetic agents administered according to this invention will of course be determined by the particular circumstances surrounding the case, including the compound administered, the route of administration, the particular condition being treated, and the similar considerations. The pharmaceutical compositions of the present invention can comprise one or more pharmaceutically acceptable excipients or carriers. The term "pharmaceutically acceptable excipients or carriers" refers to that excipients or carriers suitable for use in the pharmaceutical technology for preparing compositions with medical use.

In an embodiment, the composition is a cosmetic composition which comprises a cosmetically effective amount of the one or more crosslinked hyaluronic acids of formula (I), of formula (II) or a mixture thereof; a cosmetically effective amount of the one or more polyglycerols of formula (III) or formula (IV) or a mixture thereof; a cosmetically effective amount of one or more anesthetic agents, and optionally, one or more cosmetically acceptable excipients or carriers. The cosmetic composition of the present invention is designed to apply to the body the appropriate amount ("cosmetically effective amount") to improve its appearance or to beautify, preserve, condition, cleanse, color or protect the skin, nails, or hair (cf. Academic press Dictionary of Science and Technology, 1992, pp. 531; A terminological Dictionary of the Pharmaceutical Sciences. 2007, pp. 190). Therefore, the above cosmetic compositions are adjectivally used for a non-medical application. The term "cosmetically acceptable" or "dermatological acceptable" which is herein used interchangeably refers to that excipients or carriers suitable for use in contact with human skin without undue toxicity, incompatibility, instability, allergic response, among others.

The topical pharmaceutical or topical cosmetic compositions defined above comprise appropriate excipients or carriers for topical administration that can be pharmaceutically or cosmetically acceptable excipients, including, but not limited to, repairing cutaneous barrier function agent, a hydrating agent, an emollient, an emulsifier, a thickener, a humectant, a pH-regulating agent, an antioxidant, a preservative agent, a vehicle, or their mixtures. The excipients or carriers used have affinity for the skin, are well tolerated, stable, and are used in an amount adequate to provide the desired consistency, and ease application. Additionally, the compositions of the present invention may contain other ingredients, such as fragrances, colorants, and other components known in the state of the art for use in topical formulations. The topical compositions of the invention can be formulated in several forms that include, but are not limited to, solutions, aerosols and non-aerosol sprays, creams, powders, mousses, lotions, gels, sticks, ointments, pastes, shampoos, shower gel, body washes or face washes and emulsions.

In an embodiment, the pharmaceutical or cosmetic composition is an injectable composition. In an embodiment, the pharmaceutical or cosmetic composition is an injectable composition selected from the group consisting of intramuscular, subcutaneous, or intravenous application. In an embodiment, the pharmaceutical or cosmetic compositions of the present invention are in form of parenteral compositions suitable for their injection, infusion, or implantation into the body. The parenteral compositions defined above should be sterile, and pyrogen-free, and they can be in form of liquid such as solutions, emulsions, or suspensions, or in solid form packaged in either single-dose or multidose containers suitably diluted before use. Parenteral compositions can comprise appropriate excipients or carriers for parenteral administration that can be pharmaceutical or cosmetic excipients, including, but not limited to, solvents, suspending agents, buffering agents, substances to make the preparation isotonic with blood, stabilizers, or antimicrobial preservatives. The addition of excipients should be kept to a minimum. When excipients are used, they should not adversely affect the stability, bioavailability, safety, or efficacy of the polymers and/or the active agents, or cause toxicity or undue local irritation. There should not be any incompatibility between any of the components of the dosage form.

As it is demonstrated in the experimental section, the composition of the present invention has enhanced physical properties (rheological) and chemical properties (concentration of free polyglycerols and PPE crosslinked hydrogel) to provide an unexpectedly improvement in the amount of liposoluble (active) form of the local anesthetic and its faster release from the hydrogel matrix composition of the present invention, resulting in a reduction of the onset of the local anesthetic.

In an embodiment, the composition of the first aspect of the invention, is one having a storage modulus G' from 10 to 1500 Pa; particularly from 30 to 700 Pa measured at 1.0 Hz.

It is also a part of the present invention a process for the preparation of the first aspect of the invention. In an embodiment, the process for the preparation of the composition of the invention comprises:

when the composition comprises (a) a crosslinked hyaluronic acid of formula (I), the composition is obtainable by a process which comprises:

i) crosslinking a hyaluronic acid with a compound of formula (V)

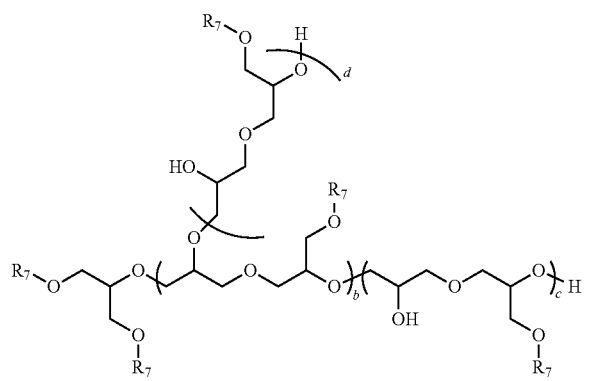

(V)

wherein:

each $R_7$ is independently selected from the group consisting of $R_2$ and $R_8$;

$R_2$ is

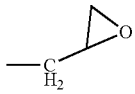

$R_8$ is

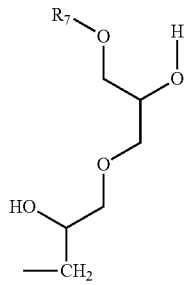

b is an integer selected from the group consisting of 1 to 70;
c is an integer selected from the group consisting of 0 to 70;
d is an integer selected from the group consisting of 0 to 70;

(ii) contacting the mixture obtained in step (i) comprising (A) one or more crosslinked hyaluronic acids of formula (I) and (B) one or more polyglycerols of formula (III) or formula (IV) with the one or more anesthetic agents (C);

(iii) optionally, contacting the mixture obtained in step (ii) with the one or more excipients or carriers (D); and (iv) optionally, sterilizing the mixture obtained in step (iii);

or alternatively, when the composition comprises (a) a crosslinked hyaluronic acid of formula (II), then the composition is obtainable by a process which comprises:

i') crosslinking a hyaluronic acid with a compound of formula (VI)

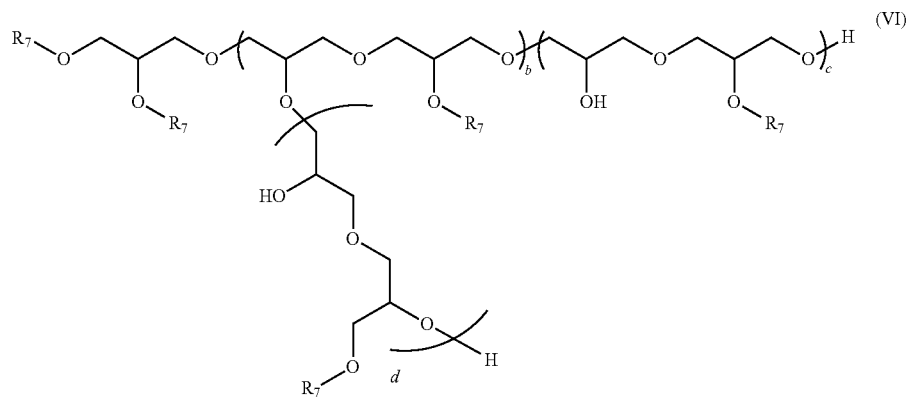

wherein:
each $R_7$ is independently selected from the group consisting of $R_2$ and $R_8$;
$R_2$ is

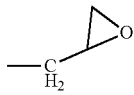

$R_8$ is

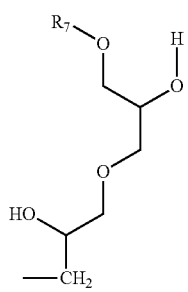

b is an integer selected from the group consisting of 1 to 70;

c is an integer selected from the group consisting of 0 to 70;
d is an integer selected from the group consisting of 0 to 70;
(ii') contacting the mixture obtained in step (i') comprising (A) one or more crosslinked hyaluronic acids of formula (II) and (B) one or more polyglycerols of formula (III) or formula (IV) with the one or more anesthetic agents (C);
(iii') optionally, contacting the mixture obtained in step (II') with the one or more excipients or carriers (D); and
(iv') optionally, sterilizing the mixture obtained in step (iii');

or alternatively,
when the composition comprises (a) a mixture of a crosslinked hyaluronic acid of formula (I) and of formula (II); then the composition is obtainable by a process which comprises:
i''') crosslinking a hyaluronic acid with a mixture comprising the compound of formula (V)

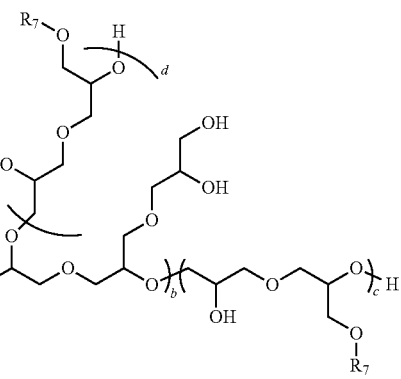

and of formula (VI)

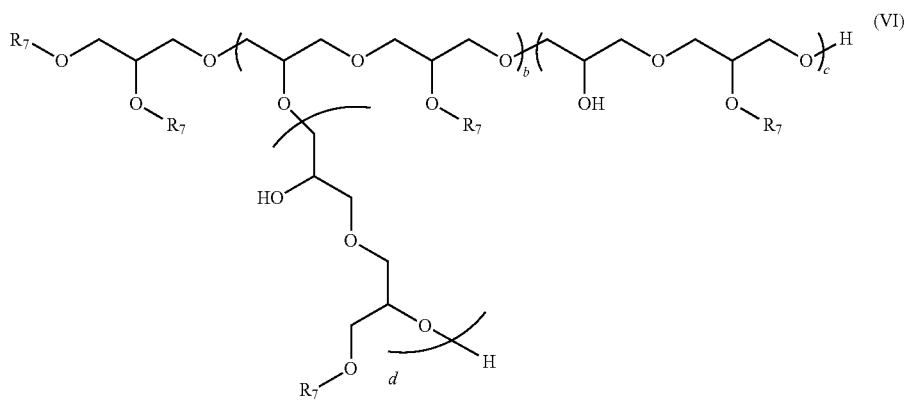

wherein:
each $R_7$ is independently selected from the group consisting of $R_2$ and $R_8$;
$R_2$ is

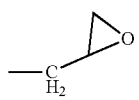

$R_8$ is

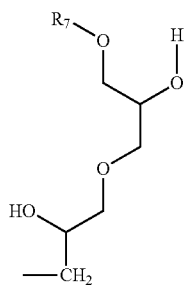

b is an integer selected from the group consisting of 1 to 70;
c is an integer selected from the group consisting of 0 to 70;
d is an integer selected from the group consisting of 0 to 70;
(ii") contacting the mixture obtained in step (I") comprising (A) one or more crosslinked hyaluronic acids of formula (I) and formula (II) and (B) one or more polyglycerols of formula (III) or formula (IV) with the one or more anesthetic agents (C);
(iii") optionally, contacting the mixture obtained in step (ii") with the one or more excipients or carriers (D); and
(iv") optionally, sterilizing the mixture obtained in step (iii").

In an embodiment, the process for the preparation of the composition of the invention comprises:
when the composition comprises (a) a crosslinked hyaluronic acid of formula (I), the composition is obtainable by a process which comprises:
i) crosslinking a hyaluronic acid with a compound of formula (V) having:
a molecular weight ($M_w$) from 204 to 15.000 Da measured by the method by size exclusion chromatography (SEC); and
an epoxy equivalent weight from 100 to 7.000 g/eq measured by ultrasonication-assisted rapid titration with HCl;
or alternatively,
when the composition comprises (a) a crosslinked hyaluronic acid of formula (II), then the composition is obtainable by a process which comprises:
i') crosslinking a hyaluronic acid with a compound of formula (VI) having:
a molecular weight ($M_w$) from 204 to 15.000 Da measured by the method by size exclusion chromatography (SEC); and
an epoxy equivalent weight from 100 to 7.000 g/eq measured by ultrasonication-assisted rapid titration with HCl;
or alternatively,
when the composition comprises (a) a mixture of a crosslinked hyaluronic acid of formula (I) and of formula (II); then the composition is obtainable by a process which comprises:
I") crosslinking a hyaluronic acid with a mixture comprising the compound of formula (V) and the compound of formula (VI) having:
a molecular weight ($M_w$) from 204 to 15.000 Da measured by the method by size exclusion chromatography (SEC); and
an epoxy equivalent weight from 100 to 7.000 g/eq measured by ultrasonication-assisted rapid titration with HCl.

In an embodiment, the process for the preparation of the composition of the invention comprises:
when the composition comprises (a) a crosslinked hyaluronic acid of formula (I), then the composition is obtainable by a process which comprises an additional step (v) after step (ii); or alternatively after step (iii), or alternatively after step (iv) comprising the addition of a compound of formula (III), a compound of formula (IV) or a mixture thereof;
or alternatively,
when the composition comprises (a) a crosslinked hyaluronic acid of formula (II), then the composition is obtainable by a process which comprises an additional step (v') after step (ii'); or alternatively after step (iii'), or alternatively after step (iv') comprising the addition of a compound of formula (III), a compound of formula (IV) or a mixture thereof;
or alternatively,
when the composition comprises (a) a mixture of a crosslinked hyaluronic acid of formula (I) and of formula (II); then the composition is obtainable by a process which comprises an additional step (v") after step (ii"); or alternatively after step (iii"), or alternatively after step (iv") comprising the addition of a compound of formula (III), a compound of formula (IV) or a mixture thereof.

In an embodiment, the process for the preparation of the composition of the invention is one wherein:
when the composition comprises (a) a crosslinked hyaluronic acid of formula (I) and the process comprises i) crosslinking a hyaluronic acid with a compound of formula (V); then the compound of formula (V) is obtained by a process comprising:
a) providing an alkaline solution containing 1,3-glycerol diglycidyl ether; and
b) maintaining the solution obtained in step a) at a temperature from 10 to 80° C. for a period from 1 min to 30 days;
or alternatively,
when the composition comprises (a) a crosslinked hyaluronic acid of formula (II) and the process comprises I') crosslinking a hyaluronic acid with a compound of formula (VI); then the compound of formula (VI) is obtained by a process comprising:
c) providing an alkaline solution containing 1,2-glycerol diglycidyl ether; and
d) maintaining the solution obtained in step c) at a temperature from 10 to 80° C. for a period from 1 min to 30 days;
or alternatively,
when the composition comprises (a) a mixture of a crosslinked hyaluronic acid of formula (I) and of formula (II); and the process comprises i") crosslinking a hyaluronic acid with a mixture comprising the compound of formula (V) and the compound of formula (VI), then:
the compound of formula (V) is obtained by a process comprising:
a) providing an alkaline solution containing 1,3-glycerol diglycidyl ether; and
b) maintaining the solution obtained in step a) at a temperature from 10 to 80° C. for a period from 1 min to 30 days; and
the compound of formula (VI) is obtained by a process comprising:
c) providing an alkaline solution containing 1,2-glycerol diglycidyl ether; and d) maintaining the solution obtained in step c) at a temperature from 10 to 80° C. for a period from 1 min to 30 days;

particularly, in step a) the alkaline solution comprises from 1 to 50 percent by weight of 1,3-glycerol diglycidyl ether; and in step c) the alkaline solution comprises from 1 to 50 percent by weight of 1,2-glycerol diglycidyl ether.

In an embodiment, the process for the preparation of the composition of the first aspect of the invention comprises:

when the composition comprises (a) a crosslinked hyaluronic acid of formula (I), the composition is obtainable by a process which further comprises an additional washing step (vi) after step (i);

or alternatively, when the composition comprises (a) a crosslinked hyaluronic acid of formula (II), then the composition is obtainable by a process which further comprises an additional washing step (vi') after step (i');

or alternatively, when the composition comprises (a) a mixture of a crosslinked hyaluronic acid of formula (I) and of formula (II); then the composition is obtainable by a process which further comprises an additional washing step (vi") after step (i").

In an embodiment, step (vi), or alternatively step (vi'); or alternatively step (vi") is performed by the addition of such appropriate amount of an acidic water solution to obtain a pH from 6.5-7.4 and a concentration of polyglycerols of formula (III) or formula (IV) or mixture thereof in the composition is from 0.45 to 25 mg/mL.

Examples of appropriate acidic water solution include, but it is not limited to strong and weak inorganic (mineral) acids such as hydrochloric acid, sulphuric acid, orthophosphoric acid, boric acid, nitric acid and strong and weak organic acids such as acetic acid, lactic acid, formic acid, citric acid, oxalic acid, uric acid, malic acid, tartaric acid, or mixture thereof. In an embodiment, all embodiments mentioned above and below of the process for the preparation of the composition of the first aspect of the invention further comprises additional step (vi), or alternatively additional step (vi'), or alternatively step (vi").

In an embodiment, step i), or alternatively step i'), or alternatively step i"), is performed at a temperature from 10 to 50° C.; particularly about 30° C. In an embodiment, step i), or alternatively step i'), or alternatively step i"), is performed for 1 to 48 h; particularly about 8 h.

In an embodiment, step ii), or alternatively step ii'), or alternatively step ii"), is performed at a temperature from 10 to 50° C.; particularly about 25° C. In an embodiment, step ii), or alternatively step ii'), or alternatively step ii"), is performed for 1 to 8 h; particularly about 2 h.

In an embodiment, if one or more excipients or carriers (D), then the process comprises step iii), or alternatively step iii'), or alternatively step iii") In an embodiment, if one or more excipients or carriers (D), then the process comprises step iii), or alternatively step iii'), or alternatively step iii") which is performed for 1 to 8 h; particularly about 2 h.

In an embodiment, the process comprises a sterilizing step iv), or alternatively step iv'), or alternatively step iv"). In an embodiment, the process comprises a sterilizing step iv), or alternatively step iv'), or alternatively step iv") which is performed at a temperature from 120 to 135° C.; particularly from 121 to 130° C. In an embodiment, the process comprises a sterilizing step iv), or alternatively step iv'), or alternatively step iv"). In an embodiment, the process comprises a sterilizing step iv), or alternatively step iv'), or alternatively step iv") which is performed at a temperature from 121 to 126° C. In an embodiment, the process comprises a sterilizing step iv), or alternatively step iv'), or alternatively step iv"). In an embodiment, the process comprises a sterilizing step iv), or alternatively step iv'), or alternatively step iv") which is performed for 1 min to 20 min; particularly for 3 min to 15 min. In an embodiment, the process comprises a sterilizing step iv), or alternatively step iv'), or alternatively step iv"). In an embodiment, the process comprises a sterilizing step iv), or alternatively step iv'), or alternatively step iv") which is performed for 10 min to 15 min. In an embodiment, the process comprises a sterilizing step iv), or alternatively step iv'), or alternatively step iv"). In an embodiment, the process comprises a sterilizing step iv), or alternatively step iv'), or alternatively step iv") which is performed at a 121° C. for 15 min. In an embodiment, the process comprises a sterilizing step iv), or alternatively step iv'), or alternatively step iv"). In an embodiment, the process comprises a sterilizing step iv), or alternatively step iv'), or alternatively step iv") which is performed at a 126° C. for 10 min. In an embodiment, the process comprises a sterilizing step iv), or alternatively step iv'), or alternatively step iv"). In an embodiment, the process comprises a sterilizing step iv), or alternatively step iv'), or alternatively step iv") which is performed at a 134° C. for 3 min.

The sterilization step can be performed according to methods well known in the state of the art. In an embodiment, the sterilization step is performed by a method selected from the group consisting of filtration, autoclaving, heating, irradiation, and combination thereof; preferably the sterilization step is performed by steam sterilized in autoclave; particularly following the pharmacopeia accepted procedures reported in the EN ISO 17665-1 (Sterilization of health care products—Moist heat Part 1: requirements for the development, validation and routine control of a sterilization process for medical device (e.g. 15 min at 121° C.). In an embodiment, the process further comprising a previous step before the sterilizing step iv), or alternatively step iv'), or alternatively step iv") which comprises conditioning the composition; particularly filling syringes with the composition of the invention. It is advantageous because the sterile composition thus obtained after steps iv), or alternatively step iv'), or alternatively step iv") is a ready-to-use sterile injectable composition. In an embodiment, the process comprises step v), or alternatively step v'), or alternatively step v").

In an embodiment, the alkaline solution of step a) or alternatively of step c) comprises a base selected from the group consisting of physiologically acceptable alkaline metal or ammonium hydroxides (Na, K), alkaline earth metal hydroxides (Mg, Ca, Sr), physiologically acceptable heavy metal hydroxides (Fe, Al, Co, Cu, Se, Zn, Cr, Ni), physiologically acceptable quaternary ammonium cations hydroxides, physiologically acceptable heavy metal or ammonium hydrogen carbonate ($NH_4$, Fe, Al, Co, Cu, Se, Zn, Cr, Ni) and mixture thereof.

The term "physiologically acceptable" refers to a non-toxic material that is compatible with a biological system such as a cell, cell culture, tissue, or organism. Preferably, the biological system is a living organism, such as a mammal, particularly a human.

In an embodiment, the alkaline solution of step a) or alternatively of step c) comprises an alkaline metal or ammonium hydroxide selected from the group consisting of potassium hydroxide (KOH), sodium hydroxide (NaOH), ammonium hydroxide and a mixture thereof; particularly sodium hydroxide.

In an embodiment, the alkaline solution of step a) or alternatively of step c) comprises an alkaline earth metal hydroxide selected from the group consisting of magnesium hydroxide, calcium hydroxide, strontium hydroxide and a mixture thereof.

In an embodiment, the alkaline solution of step a) or alternatively of step c) comprises a heavy metal hydroxide selected from the group consisting of iron hydroxide, aluminium hydroxide, cobalt hydroxide, selenium hydroxide, tin hydroxide, chromium hydroxide, nickel hydroxide and a mixture thereof.

In an embodiment, the alkaline solution of step a) or alternatively of step c) comprises a quaternary ammonium hydroxides of formula $HONR_6R_7R_8R_9$ wherein each one of $R_6$, $R_7$, $R_8$ and $R_9$ is independently selected from the group consisting of ($C_1$-$C_8$) alkyl, or alternatively two of $R_5$, $R_6$, $R_7$ and $R_9$ form a ($C_5$-$C_6$) cycloalkyl ring.

In an embodiment, the alkaline solution of step a) or alternatively of step c) comprises heavy metal or ammonium hydrogen carbonate selected from the group consisting of iron hydrogen carbonate, aluminium hydrogen carbonate, cobalt hydrogen carbonate, Cupper hydrogen carbonate, selenium hydrogen carbonate, zinc hydrogen carbonate, chromium hydrogen carbonate, nickel hydrogen carbonate, ammonium hydrogen carbonate and a mixture thereof; particularly sodium hydrogen carbonate.

In an embodiment, the alkaline solution of step a) or alternatively of step c) comprises from 1 to 50 percent by weight of 1,3-GDE or alternatively of 1,2-GDE. In an embodiment, the alkaline solution of step a) or alternatively of step c) comprises an alkaline hydroxide and comprises from 1 to 50 percent by weight of 1,3-GDE or alternatively of 1,2-GDE. In an embodiment, the alkaline solution of step a) or alternatively of step c) comprises an alkaline hydroxide selected from the group consisting of potassium hydroxide (KOH), sodium hydroxide (NaOH) and a mixture thereof and comprises from 1 to 50 percent by weight of 1,3-GDE or alternatively of 1,2-GDE. In an embodiment, the alkaline solution of step a) or alternatively of step c) comprises sodium hydroxide (NaOH) and comprises from 1 to 50 percent by weight of 1,3-GDE or alternatively of 1,2-GDE. The 1,3-GDE and 1,2-GDE have been previously disclosed in the state of the art, and they are commercially available (cf. experimental section).

In an embodiment, step a) or alternatively step c) of the process of the invention is performed at room temperature. The term "room temperature" refers to a temperature at about 25 to 35° C. In an embodiment, step a) or alternatively step c) of the process of the invention is performed in the presence of a solvent. In an embodiment, step a) or alternatively step c) of the process of the invention is performed in the presence of a solvent selected from the group consisting of water, ($C_1$-$C_4$) alkyl-OH, ($C_1$-$C_4$) alkyl-CO—($C_1$-$C_4$) alkyl, ($C_1$-$C_4$) alkyl-CO—O—($C_1$-$C_4$) alkyl, ($C_1$-$C_4$) alkyl-CN, and mixtures thereof. In an embodiment, step a) or alternatively step c) of the process of the invention is performed in the presence of a solvent selected from the group consisting of methanol, ethanol, 1-propanol, 2-propanol, acetone, acetonitrile, ethyl acetate and mixture thereof; particularly the solvent is water.

The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, and tert-butyl.

In an embodiment, step b) or alternatively step d) is performed by submitting the 1,3-GDE or alternatively the 1,2-GDE at a temperature from 10 to 80° C. for a period from 1 min to 30 days during which self-polymerization of GDE take places.

In an embodiment, step b) or alternatively step d) is performed by submitting the 1,3-GDE or alternatively the 1,2-GDE at a temperature in the range from 50 to 80° C. for a period from 1 minute to 500 minutes. In an embodiment, step b) or alternatively step d) is performed by submitting the 1,3-GDE or alternatively the 1,2-GDE at a temperature in the range from 50 to 80° C. for a period from 5 to 60 minutes.

In an embodiment, step b) or alternatively step d) is performed by submitting the 1,3-GDE or alternatively the 1,2-GDE at a temperature in the range from 10 to 40° C. for a period from 1 day to 30 days. In an embodiment, step b) or alternatively step d) is performed by submitting the 1,3-GDE or alternatively the 1,2-GDE at a temperature from 10 to 40° C. for a period from 2 day to 7 days.

It is also part of the present invention a composition of the first aspect of the invention obtainable by the process as defined above. For the purposes of the invention the expressions "obtainable", "obtained" and equivalent expressions are used interchangeably, and in any case, the expression "obtainable" encompasses the expression "obtained". All embodiments disclosed above for the process for the preparation and also for the composition per se also apply to the composition obtainable by the process of the invention.

It is also a part of the invention the use of the composition of the first aspect of the invention.

The composition of the first aspect of the invention can be used in the pharmaceutical field. In an embodiment, the composition of the invention is a pharmaceutical composition as defined above for use in therapy. In an embodiment, the composition of the invention is a pharmaceutical composition as defined above for use in the treatment of a disease or condition that involves a deficit and/or impairment of hyaluronic acid. In an embodiment, the composition of the invention is a pharmaceutical composition as defined above for use in the treatment of a disease or condition that involves a deficit and/or impairment of hyaluronic acid selected from the group consisting of joint and bones diseases such as osteoarthritis, facial and body hypovolumetries, facial and body asymmetries; wound healing, detached retina or other eye injuries, tissues and mucosa inflammation, ear and sinus infections, and to reduce burning, itching, and painful that occur with thinning tissues and mucosa.

This aspect could be also formulated as the use of the pharmaceutical composition of the first aspect of the invention as defined above for the preparation of a medicament. It also relates to a method for the treatment of a mammal suffering or susceptible of suffer a disease or condition involving a deficit and/or impairment of hyaluronic acid, such as those mentioned above. This aspect could be also formulated as the use of the pharmaceutical composition of the invention for the preparation of a medicament for the treatment of a disease or condition involving a deficit and/or impairment of hyaluronic acid, such as those mentioned above.

The composition of the first aspect of the invention can be used in the cosmetic field. In an embodiment, the composition of the invention is a cosmetic composition as defined above useful as skin care agent. The term "skin care agent" encompasses an agent capable of ameliorating at least one of the following symptoms: roughness, flakiness, dehydration, tightness, chapping, and lack of elasticity. In an embodiment, the composition of the invention is a cosmetic composition as defined above useful as dermal filler (also known as soft tissue augmentation agent) as skin care agent.

It is also a part of the invention, the use of a composition of the first aspect of the invention as a carrier. In an embodiment, the composition of the first aspect of the invention is a drug delivery system; particularly as a delivery system of pharmaceutical active ingredients, diagnostic agents, cosmetic compounds, peptides, proteins, antibodies, vaccines, polynucleotides, vitamins, antioxidants, and genes.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

List of Abbreviations

HA: hyaluronic acid
GAG: glycosaminoglycan
C.D.: cross-linking degree
GlcA: D-glucuronic acid
GlcNAc: N-acetyl-D-glucosamine
ECM: extracellular matrix
HYAL: hyaluronidase enzyme
IA: inflammatory arthritis
BDDE: 1,4-butane diol diglycidyl ether
GDE: 1,3-glycerol diglycidyl ether
PPE: polyglycerol diglycidyl ether
FDA: Food and Drug Administration
EEW: Epoxy Equivalent Weight
GC/MS: Gas Chromatography coupled with Mass detector
SEC/UV/MS: Size Exclusion Chromatography coupled with Ultraviolet and Mass detector
UV-Vis: Ultraviolet and Visible spectroscopy
PBS: phosphate buffer solution
IPN: interpenetrating networks
Mw: weight-average molecular weight;
Mn: number-average molecular weight;
LA: Local Anesthetic;
Gly: Glycerol
Mann: Mannitol
LIDO: lidocaine hydrochloride;
ARTI: articaine hydrochloride;
MEPI: mepivacaine hydrochloride.

Materials

SHYALT Ultrapure Sodium Hyaluronate (Hyaluronic Acid) from Altergon Italy.

1,3-Bis(2-oxiranylmethoxy)-2-propanol which is also known with the following names, tradenames, synonyms, and abbreviations: 1,3-Bis(oxiran-2-ylmethoxy) propan-2-ol; 2-Propanol, 1,3-bis(oxiranylmethoxy); Glycerol 1,3-diglycidyl ether; Denacol EX-313, MW=204 Da, EEW=141 g/eq from Nagase Chemtex; 1,3-Glycerol Diglycidyl Ether, MW=204 Da from Merck; and 1,3-GDE has the following structure:

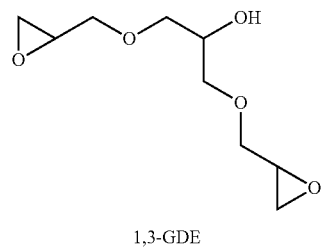 [SMILES: OC(COCC1CO1)COCC1CO1]

1,3-GDE 2,3-Bis(2-oxiranylmethoxy)-1-propanol which is also known with the following names, tradenames, synonyms, and abbreviations 2,3-bis(oxiran-2-ylmethoxy) propan-1-ol: 1-Propanol, 1,2-bis(oxiranylmethoxy); Glycerol 1,2-diglycidyl ether; 1,2-Glycerol diglycidyl ether, MW=204 Da from Merck; and 1,2-GDE has the following structure:

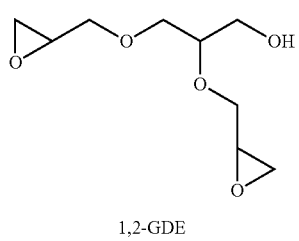 [SMILES: OCC(COCC1CO1)OCC1CO1]

1,2-GDE

Mixtures of 1,3-GDE and 1,2-GDE are also commercially available with the following trademark names: Denacol EX-314, MW=260 Da, EEW=144 g/eq from Nagase Chemtex.

The following compounds were purchased from Merck: butane Diol Diglycidyl Ether (BDDE), MW=202 Da; sodium Hydroxide pellets (NaOH); hydrochloric Acid 37% (HCl); sodium Chloride powder (NaCl); Potassium Chloride powder (KCl); phosphoric acid 85% ($H_3PO_4$); phosphate buffer saline (PBS) pellets; distilled water ($H_2O$); glycerol; mannitol; lidocaine hydrochloride (LIDO); articaine hydrochloride (ARTI); mepivacaine hydrochloride (MEPI).

Analytical Methods

Quantitative method for the determination of neutral fraction and total amount of Local Anesthetics was evaluated by UV-Vis spectrophotometer. Quantitative method for the measurement of the semi-volatile compounds was evaluated by GC/MS chromatographic instrument for the neutral fraction of Local Anesthetics. LC refers to methods that implies a liquid chromatography technique, which historically are termed using different acronyms such as High-Performance Liquid chromatography (HPLC), Gel Permeation Chromatography (GPC), Size Exclusion Chromatography (SEC), etc. depending of used columns or the chemical nature of the mobile phase (aqueous or organic). The International Union of Pure and Applied Chemists (IUPAC) prefer to use the term SEC for experiments of this type. Combination of different detectors such as Ultra Violet (UV), UV-visible (UV-vis), Mass (MS), refractive index (RI), light scattering (LS), etc. coupled with the column are also possible, depending of the chemical nature of the analyte to be detected and quantified. Quantitative method for the measurement of the non-volatile compounds was evaluated by size exclusion chromatography coupled with UV-visible and Mass detector SEC/UV/MS chromatographic instrument for the total amount of Local Anesthetics. Quantitative method for the measurement of the average weight average molecular weight (Mw), Number average molecular weight (Mn) and polydispersity (Mw/Mn) was evaluated by size exclusion chromatography coupled with light scattering detector SEC/LS. Quantitative method for the measurement of the epoxy equivalent weight (EEW) was evaluated by ultrasonic assisted titration. Quantitative method for the measuring pH was calculated by direct reading of pHmeter equipped with an electrode the PPE obtained following the process as defined above was analytically monitored over time using respectively GPC instrument equipped with light scattering detector and quantitative titration with HCl as previously described. Before each analysis, the self-polymerization reaction of GDE was stopped by adding 1M hydrochloric acid solution and PBS to neutralize alkaline catalyst and restore the pH of the Polyglycerol Polyglycidyl Ether solution to 7.0.

Values of the average molecular weight (MW) and EEW of the obtained polyglycerol polyglycidyl ether (PPE) for each combination of temperature and time are reported in table 1.

TABLE 1

| PPE Number | [1,3-GDE] (% w/w) | [NaOH] (mol/L) | Temp. (° C.) | Time (min) | PPE average MW (g/mol) | PPE EEW (g/eq) | Epoxides (meq/g) |
|---|---|---|---|---|---|---|---|
| PPE 1 | 10.00 | 1.00 | 20 | 3 | 3736 | 581 | 1.720 |
| PPE 2 | 10.00 | 1.00 | 30 | 1 | 2449 | 408 | 2.450 |
| PPE 3 | 10.00 | 1.00 | 30 | 0.5 | 937 | 234 | 4.268 |
| PPE 4 | 10.00 | 0.50 | 20 | 1 | 684 | 155 | 6.556 |
| PPE 5 | 10.00 | 0 | 20 | 3 | 204 | 102 | 9.780 | directly immersed in the hydrogel. Quantitative method for the measuring Osmolality was calculated by direct reading of osmometer equipped with the probe directly immersed in the hydrogel.

To sum up, the International Union of Pure and Applied Chemists (IUPAC) nomenclature has been used for identifying the method of measuring by liquid chromatography. Therefore, for the purpose of the present invention, terms liquid chromatography (LC), High-Performance Liquid chromatography (HPLC), Gel Permeation Chromatography (GPC), Size Exclusion Chromatography (SEC) are considered equivalents and have been referred all of them as Size Exclusion Chromatography (SEC) for clarification 1. Local Anesthetic and Polyglycerol Polyglycidyl Ether (PPE) Crosslinked-Hyaluronic Acid Conjugate
1.1. Polyglycerol Polyglycidyl Ether (PPE)
1.1. Using 1,3-GDE as Stating Material The below-mentioned preparation processes can be also performed by using the Denacol® EX-313 commercially available from Nagase as a source of 1,3-GDE. Nevertheless, these processes can be also performed by using the 1,3-glycerol diglycidyl ether commercially available from Merck or with the trademark Denacol® EX-314 which is a mixture containing 1,3-DGE instead of Denacol® EX-313.

1.1.1. Preparation Process of PPEs

Sodium hydroxide pellets (NaOH) were dissolved in water to form an alkaline solution containing a 4 percent of NaOH (1M) by weight based on total solution weight (Solution A).

1,3-GDE (Denacol® EX-313) was dissolved at room temperature in a portion of solution A to form an alkaline solution containing from 1 to 50 percent of 1,3-GDE by weight based on total solution weight (Solution C1). Solution C1 was then left to react at controlled temperature in the range between 10 and 80° C. for a period comprised from 1 min to 30 days during which self-polymerization of 1,3-GDE take place giving Polyglycerol Polyglycidyl Ethers disclosed in Table 1 (Examples 1-5).

1.1.2. Characterization of the PPEs

The weigh average molecular weight (Mw) and the epoxy content of the obtained PPE, measured as Epoxy Equivalent Weight expressed as percentage of EEW of starting GDE, of 1.2. Conjugate of Local Anesthetic with PPE Crosslinked Hyaluronic Acid
1.2.1. Non Sterilized Conjugate
1.2.1.1. Preparation Process
1.2.1.1.1. Preparation Process of PPE Crosslinked Hyaluronic Acid PPE crosslinked hyaluronic acids were prepared following the process as defined below:
Step A. Preparation of the PPE 1-5 Following the Process Disclosed Above.
Step B: Preparation of Crosslinked Hyaluronic Acid Alternative B1: Hyaluronic acid (HA) dry powder was gently dissolved at room temperature (25° C.) in a portion of solution A (or directly added to solution C3) to form an alkaline solution containing from 5 to 15 percent of hydrated HA by weight based on total solution weight (Solution B).

The solution C3 is then added to the solution B to provide an alkaline solution with a hydroxide concentration in the final solution in the range from 0.25 and 0.75M and with a ratio of HA and PPE from 2 to 12.5% w/w (expressed as weight ratio of PPE to dry polysaccharide).

Alternative B2: The solution C3 is then added to the solution B to provide an alkaline solution with a hydroxide concentration in the final solution in the range from 0.25 and 0.75M, a concentration of HA in the final solution in the range from 8 to 10% by weight in relation to the total weight, and a concentration of PPE in the final solution in the range from 0.2 to 1% by weight in relation to the total weight. The ratio expressed as weight ratio of PPE to dry polysaccharide is from 2 to 40% w/w expressed as weight ratio of PPE to dry polysaccharide.

The resulting alkaline solution consisting of hyaluronic acid (HA), PPE and NaOH is then thoroughly mixed at room temperature. The homogenous solution was then left to react at controlled temperature in the range between 20 and 50° C. for a period comprised from 1 to 48 hours.

Step C: Purification and Isolation of the Crosslinked Polysaccharide

The PPE cross-linked hyaluronic acid (hydrogel) was then washed with acidic water solution (1M hydrochloric acid and PBS) from 48 to 120 hours to remove unreacted materials and by-products, to neutralize alkaline catalyst and restore the pH of the PPE cross-linked hyaluronic acid (hydrogel) to 6.5-7.4 by ion exchange and to reach the desired final concentration of HA in the PPE cross-linked hyaluronic acid hydrogel from 1 to 50 mg/mL as shown in Tables below.

At fixed check points (i.e. at 12, 24, 36, 48 hours), a portion (1 gram) of the hydrogel was removed and analyzed using the same techniques used for determination of parameters of the final products reported in tables 2-15 below. In particular, the concentration of free polyglycerols in the PPE cross-linked HA expressed in mg/mL, and their chemical structure were evaluated by SEC/UV/MS.

1.2.1.1.2. Addition of the Local Anesthetic to the PPE Crosslinked Hyaluronic Acid The one or more local anesthetic agents as hydrochloride salt dry powder were gently dissolved at room temperature (25° C.) in a portion of phosphate buffered saline solution to form a local anesthetic solution containing from 1 to 20 percent of local anesthetic by weight based on total solution weight having acceptable physiological pH (Solution D).

The solution D is then added and mixed to the washed PPE cross-linked hyaluronic acid hydrogel obtained in previous section to reach the desired final concentration of HA and local anesthetic (LA) in the PPE cross-linked hyaluronic acid hydrogel respectively from 1 to 50 mg/mL for the HA and from 0.1 to 10 mg/mL for the Local Anesthetic.

The PPE cross-linked hyaluronic acid (hydrogel) containing the local anesthetic could be optionally dehydrated under vacuum at 30° C. or lyophilized (freeze-dried) and stored for following use or analysis.

1.2.2. Sterilized Conjugate 1.2.2.1. Preparation Process

The PPE cross-linked hyaluronic acid (hydrogel) obtained in previous section containing the local anesthetic was filled into syringes and steam sterilized in autoclave following the pharmacopeia accepted procedures reported in the EN ISO 17665-1, Sterilization of health care products—Moist heat Part 1: requirements for the development, validation, and routine control of a sterilization process for medical device (e.g. 15 min at) 121° C.

The PPE cross-linked hyaluronic acid (hydrogel) containing the local anesthetic could be optionally dehydrated under vacuum at 30° C. or lyophilized (freeze-dried) and stored for following use or analysis.

1.2.2.2. Characterization of the PPE Crosslinked Hyaluronic Acid Ex. 1-70

The chemical composition of the sterilized and non-sterilized conjugates of PPE cross-linked hyaluronic acid and local anesthetic (lidocaine, mepivacaine, and articaine) (as prepared above are disclosed in Tables 2-7.

TABLE 2

NON-STERILIZED conjugate containing PPE cross-linked HA and LIDOCAINE

| Ex. | Conc. HA[a] | Cross-linker | C.D. (%) | Conc. free PG[b] | Free PG MW range | pH | Conc LA[c] | % B[d] | pKa[s] |
|---|---|---|---|---|---|---|---|---|---|
| 1 | 25 | PPE 1 | 0.2003 | 2.126 | 1129 ÷ 3129 | 7.4 | 3 | 59.03 | 7.24 |
| 2 | 25 | PPE 2 | 0.2657 | 0.650 | 611 ÷ 1944 | 7.4 | 3 | 50.91 | 7.38 |
| 3 | 25 | PPE 3 | 0.3419 | 0.374 | 314 ÷ 1129 | 7.4 | 3 | 44.29 | 7.50 |
| 4 | 15 | PPE 4 | 0.1607 | 0.217 | 314 ÷ 1129 | 7.4 | 3 | 43.09 | 7.52 |
| 5 | 25 | PPE 4 | 0.3512 | 0.343 | 314 ÷ 1129 | 7.4 | 3 | 37.23 | 7.63 |
| 6 | 15 | PPE 5 | 0.1636 | 0.193 | 314 ÷ 1129 | 7.4 | 3 | 46.40 | 7.46 |
| 7 | 25 | PPE 5 | 0.3555 | 0.323 | 314 ÷ 1129 | 7.4 | 3 | 44.52 | 7.50 |
| 8 | 25 | PPE 5 | 0.3576 | 0.341 | 314 ÷ 1129 | 7.0 | 3 | 16.80 | 7.69 |
| 9 | 15 | PPE 3 | 0.1575 | 0.225 | 314 ÷ 1129 | 7.4 | 3 | 38.73 | 7.60 |
| 10 | 20 | PPE 3 | 0.2431 | 0.306 | 314 ÷ 1129 | 7.4 | 3 | 40.77 | 7.56 |
| 11 | 30 | PPE 3 | 0.4369 | 0.409 | 314 ÷ 1129 | 7.4 | 3 | 44.61 | 7.49 |
| 12 | 25 | PPE 3 | 0.3461 | 0.374 | 314 ÷ 1129 | 7.4 | 1 | 45.29 | 7.48 |
| 13 | 25 | PPE 3 | 0.3398 | 0.374 | 314 ÷ 1129 | 7.4 | 9 | 41.40 | 7.55 |
| 14 | 25 | PPE 3 | 0.3400 | 0.374 | 314 ÷ 1129 | 7.2 | 3 | 30.02 | 7.57 |
| 15 | 25 | PPE 3 | 0.3453 | 0.374 | 314 ÷ 1129 | 7.0 | 3 | 19.83 | 7.61 |

TABLE 3

STERILIZED conjugate containing PPE cross-linked HA and LIDOCAINE

| Ex. | Conc. HA[a] | Cross-linker | C.D. (%) | Conc. free PG[b] | Free PG MW range | pH | Conc LA[c] | % B[d] | pKa[s] |
|---|---|---|---|---|---|---|---|---|---|
| 16 | 25 | PPE 1 | 0.1624 | 2.497 | 1129 ÷ 2310 | 7.4 | 3 | 62.41 | 7.18 |
| 17 | 25 | PPE 2 | 0.2163 | 0.774 | 611 ÷ 1629 | 7.4 | 3 | 54.44 | 7.32 |
| 18 | 25 | PPE 3 | 0.2779 | 0.452 | 314 ÷ 759 | 7.4 | 3 | 48.70 | 7.44 |
| 19 | 15 | PPE 4 | 0.1337 | 0.266 | 314 ÷ 759 | 7.4 | 3 | 46.58 | 7.46 |
| 20 | 25 | PPE 4 | 0.2850 | 0.426 | 314 ÷ 759 | 7.4 | 3 | 40.59 | 7.57 |
| 21 | 15 | PPE 5 | 0.1357 | 0.243 | 314 ÷ 759 | 7.4 | 3 | 49.93 | 7.40 |
| 22 | 25 | PPE 5 | 0.2882 | 0.412 | 314 ÷ 759 | 7.4 | 3 | 48.04 | 7.43 |
| 23 | 25 | PPE 5 | 0.2904 | 0.412 | 314 ÷ 759 | 7.0 | 3 | 18.87 | 7.63 |
| 24 | 15 | PPE 3 | 0.1317 | 0.276 | 314 ÷ 759 | 7.4 | 3 | 42.13 | 7.54 |
| 25 | 20 | PPE 3 | 0.1984 | 0.380 | 314 ÷ 759 | 7.4 | 3 | 44.22 | 7.50 |
| 26 | 30 | PPE 3 | 0.3606 | 0.515 | 314 ÷ 759 | 7.4 | 3 | 48.13 | 7.43 |
| 27 | 25 | PPE 3 | 0.2701 | 0.452 | 314 ÷ 759 | 7.4 | 1 | 48.81 | 7.42 |
| 28 | 25 | PPE 3 | 0.2856 | 0.452 | 314 ÷ 759 | 7.4 | 9 | 35.58 | 7.66 |
| 29 | 25 | PPE 3 | 0.2701 | 0.452 | 314 ÷ 759 | 7.2 | 3 | 33.07 | 7.51 |
| 30 | 25 | PPE 3 | 0.2856 | 0.452 | 314 ÷ 759 | 7.0 | 3 | 22.17 | 7.55 |

TABLE 4

NON-STERILIZED conjugate containing PPE cross-linked HA and MEPIVACAINE

| Ex. | Conc. HA[a] | Cross-linker | C.D. (%) | Conc. free PG[b] | Free PG MW range | pH | Conc LA[c] | % B[d] | pKa[s] |
|---|---|---|---|---|---|---|---|---|---|
| 31 | 25 | PPE 1 | 0.2003 | 2.126 | 1129 ÷ 3129 | 7.4 | 3 | 60.56 | 7.21 |
| 32 | 25 | PPE 2 | 0.2657 | 0.650 | 611 ÷ 1944 | 7.4 | 3 | 52.74 | 7.35 |
| 33 | 25 | PPE 3 | 0.3419 | 0.374 | 314 ÷ 1129 | 7.4 | 3 | 49.41 | 7.41 |
| 34 | 15 | PPE 3 | 0.1575 | 0.225 | 314 ÷ 1129 | 7.4 | 3 | 41.71 | 7.55 |
| 35 | 20 | PPE 3 | 0.2431 | 0.306 | 314 ÷ 1129 | 7.4 | 3 | 41.82 | 7.54 |
| 36 | 30 | PPE 3 | 0.4369 | 0.409 | 314 ÷ 1129 | 7.4 | 3 | 47.51 | 7.44 |
| 37 | 25 | PPE 3 | 0.3461 | 0.374 | 314 ÷ 1129 | 7.4 | 1 | 49.47 | 7.41 |
| 38 | 25 | PPE 3 | 0.3398 | 0.374 | 314 ÷ 1129 | 7.4 | 9 | 44.51 | 7.50 |
| 39 | 25 | PPE 3 | 0.3400 | 0.374 | 314 ÷ 1129 | 7.2 | 3 | 33.83 | 7.49 |
| 40 | 25 | PPE 3 | 0.3453 | 0.374 | 314 ÷ 1129 | 7.0 | 3 | 22.38 | 7.54 |

TABLE 5

STERILIZED conjugate containing PPE cross-linked HA and MEPIVACAINE

| Ex. | Conc. HA[a] | Cross-linker | C.D. (%) | Conc. free PG[b] | Free PG MW range | pH | Conc LA[c] | % B[d] | pKa[s] |
|---|---|---|---|---|---|---|---|---|---|
| 41 | 25 | PPE 1 | 0.1627 | 2.497 | 1129 ÷ 2310 | 7.4 | 3 | 64.74 | 7.14 |
| 42 | 25 | PPE 2 | 0.2163 | 0.774 | 611 ÷ 1629 | 7.4 | 3 | 57.17 | 7.27 |
| 43 | 25 | PPE 3 | 0.2779 | 0.452 | 314 ÷ 759 | 7.4 | 3 | 53.88 | 7.33 |
| 44 | 15 | PPE 3 | 0.1317 | 0.276 | 314 ÷ 759 | 7.4 | 3 | 46.11 | 7.47 |
| 45 | 20 | PPE 3 | 0.1984 | 0.380 | 314 ÷ 759 | 7.4 | 3 | 46.23 | 7.47 |
| 46 | 30 | PPE 3 | 0.3606 | 0.515 | 314 ÷ 759 | 7.4 | 3 | 51.98 | 7.37 |
| 47 | 25 | PPE 3 | 0.2701 | 0.452 | 314 ÷ 759 | 7.4 | 1 | 53.94 | 7.33 |
| 48 | 25 | PPE 3 | 0.2856 | 0.452 | 314 ÷ 759 | 7.4 | 9 | 48.96 | 7.42 |
| 49 | 25 | PPE 3 | 0.2701 | 0.452 | 314 ÷ 759 | 7.2 | 3 | 37.95 | 7.41 |
| 50 | 25 | PPE 3 | 0.2856 | 0.452 | 314 ÷ 759 | 7.0 | 3 | 25.65 | 7.46 |

TABLE 6

NON-STERILIZED conjugate containing PPE cross-linked HA and ARTICAINE

| Ex. | Conc. HA[a] | Cross-linker | C.D. (%) | Conc. free PG[b] | Free PG MW range | pH | Conc LA[c] | % B[d] | pKa[s] |
|---|---|---|---|---|---|---|---|---|---|
| 51 | 25 | PPE 1 | 0.2003 | 2.126 | 1129 ÷ 3129 | 7.4 | 3 | 67.81 | 7.08 |
| 52 | 25 | PPE 2 | 0.2657 | 0.650 | 611 ÷ 1944 | 7.4 | 3 | 64.43 | 7.14 |
| 53 | 25 | PPE 3 | 0.3419 | 0.374 | 314 ÷ 1129 | 7.4 | 3 | 56.79 | 7.28 |
| 54 | 15 | PPE 3 | 0.1575 | 0.225 | 314 ÷ 1129 | 7.4 | 3 | 53.74 | 7.33 |
| 55 | 20 | PPE 3 | 0.2431 | 0.306 | 314 ÷ 1129 | 7.4 | 3 | 56.85 | 7.28 |
| 56 | 30 | PPE 3 | 0.4369 | 0.409 | 314 ÷ 1129 | 7.4 | 3 | 60.23 | 7.22 |
| 57 | 25 | PPE 3 | 0.3461 | 0.374 | 314 ÷ 1129 | 7.4 | 1 | 61.28 | 7.20 |
| 58 | 25 | PPE 3 | 0.3398 | 0.374 | 314 ÷ 1129 | 7.4 | 9 | 56.57 | 7.29 |
| 59 | 25 | PPE 3 | 0.3400 | 0.374 | 314 ÷ 1129 | 7.2 | 3 | 40.94 | 7.36 |
| 60 | 25 | PPE 3 | 0.3453 | 0.374 | 314 ÷ 1129 | 7.0 | 3 | 28.18 | 7.41 |

TABLE 7

STERILIZED conjugate containing PPE cross-linked HA and ARTICAINE

| Ex. | Conc. HA[a] | Cross-linker | C.D. (%) | Conc. free PG[b] | Free PG MW range | pH | Conc LA[c] | % B[d] | pKa[s] |
|---|---|---|---|---|---|---|---|---|---|
| 61 | 25 | PPE 1 | 0.1624 | 2.497 | 1129 ÷ 2310 | 7.4 | 3 | 70.07 | 7.03 |
| 62 | 25 | PPE 2 | 0.2163 | 0.774 | 611 ÷ 1629 | 7.4 | 3 | 66.81 | 7.10 |
| 63 | 25 | PPE 3 | 0.2779 | 0.452 | 314 ÷ 759 | 7.4 | 3 | 59.36 | 7.24 |
| 64 | 15 | PPE 3 | 0.1317 | 0.276 | 314 ÷ 759 | 7.4 | 3 | 56.36 | 7.29 |
| 65 | 20 | PPE 3 | 0.1984 | 0.380 | 314 ÷ 759 | 7.4 | 3 | 59.42 | 7.23 |
| 66 | 30 | PPE 3 | 0.3606 | 0.515 | 314 ÷ 759 | 7.4 | 3 | 62.73 | 7.17 |
| 67 | 25 | PPE 3 | 0.2701 | 0.452 | 314 ÷ 759 | 7.4 | 1 | 63.75 | 7.15 |
| 68 | 25 | PPE 3 | 0.2856 | 0.452 | 314 ÷ 759 | 7.4 | 9 | 59.14 | 7.24 |
| 69 | 25 | PPE 3 | 0.2701 | 0.452 | 314 ÷ 759 | 7.2 | 3 | 43.51 | 7.31 |
| 70 | 25 | PPE 3 | 0.2856 | 0.452 | 314 ÷ 759 | 7.0 | 3 | 30.65 | 7.35 |

(a) Concentration of HA in the PPE cross-linked HA conjugate expressed as mg/mL.
(b) Concentration of free polyglycerols in the PPE cross-linked HA expressed in mg/mL, and their chemical structure were evaluated by SEC/UV/MS.
(c) Concentration of (local anesthetic) LA in the PPE cross-linked HA expressed in mg/mL, evaluated by GC/MS and by SEC/UV/MS.
(d) the percentage of neutral form B of the local anesthetic (determined using GC/MS) over the total amount of local anesthetic B+BH$^+$ (determined using SEC/UV/MS) in the conjugate containing PPE cross-linked HA and local anesthetic were calculated, either for the non-sterilized and sterilized for 15 min at 121° C.

To sum up, the PPE cross-linked HA conjugate of the present invention were obtained using the PPE at different MW and EEW as reported in table 1. The PPE cross-linked HA conjugate ranged from 15 to 30 mg/mL of crosslinked hyaluronic acid concentration, which means showing different crosslinking degrees disclosed in corresponding tables above. As it is mentioned above, the PPE cross-linked HA conjugate contains polyglycerols whose MW and concentration were measured by SEC/UV/MS. Further, the PPE cross-linked HA conjugate of the present invention contains a percentage of neutral form B of local anesthetic much higher than the predicted thermodynamic value from Henderson-Hasselbalch equation, e.g. at pH 7.4.

Therefore, the $pKa^S$ experimentally calculated for the local anesthetic at a fixed pH value calculated by means of the Henderson-Hasselbalch equation, using experimental concentrations of B and BH$^+$ are much lower than the thermodynamic pKa.

The experimental data of % of B in comparison with the predicted % of B is summarized in the following table:

| | Conjugate of PPE crosslinked hyaluronic acid and local anesthetic | | | |
|---|---|---|---|---|
| | B form (%) by weight | | pKa | |
| Local anesthetic | Experimentally calculated | Predicted value$^{(a)}$ | $pKa^S$ | $pKa^T$ |
| lidocaine | 37.23-62.41 | 24.03 | 7.18-7.69 | 7.9 |
| mepivacaine | 41.71-64.74 | 28.47 | 7.14-7.55 | 7.8 |
| articaine | 53.74-70.07 | 38.69 | 7.03-7.41 | 7.6 |

$^{(a)}$Predicted value from Henderson-Hasselbalch equation, e.g., at pH 7.4.
$pKa^S$ corresponds to apparent pKa experimentally calculated.
$pKa^T$ corresponds to thermodynamic pKa For all explored local aesthetics, but without limitations in their chemical structure, unexpectedly the bioavailable neutral form B in the PPE crosslinked hyaluronic acid hydrogel, show a percentage much higher than the predicted, due to stabilization of this form by several factors. In fact, as it is shown in the experimental data herein above (cf. Tables 2-7), the thermodynamic pKa value (calculated from the ratio B/BH+) is decreased from 2.5% to 10% of its predicted value. In other words, for each Local Anesthetic contained in the hydrogel of the present invention, its experimental pKa is from 2.5% to 10% lower than the respectively predicted thermodynamic pKa. From the point of view of the neutral bioavailable form of local anesthetic agent, the B form is increased from 40% to 160% of its value know in the state of the art (predicted thermodynamic pKa value).

Therefore, without being to any theory, it seems that the stabilization of the neutral form B appears correlated with the amphiphilic character of the hyperbranched PPE used as crosslinker, its molecular weight and the crosslinking degree, the concentration and molecular weight of the free polyglycerols deriving from natural hydrolysis in a complex relationship due to the synergic effect between these factors.

2.1.3. Comparative Conjugate of Local Anesthetic with BDDE Crosslinked Hyaluronic Acid (Comparative Ex. 71-150)

The comparative conjugates BDDE crosslinked hyaluronic acid and local anesthetic are those prepared from BDDE instead of PPE and the further addition of glycerol or mannitol to the conjugate thus obtained.

2.1.3.1. Preparation Process

Sodium hydroxide pellets (NaOH) were dissolved in water to form an alkaline solution containing a 4 percent of NaOH (1M) by weight based on total solution weight (Solution A). Hyaluronic acid was gently dissolved at room temperature (25° C.) in a portion of solution A to form an alkaline solution containing from 5 to 15 percent of hydrated HA by weight based on total solution weight (Solution B).

BDDE was dissolved at room temperature in a distilled water to form a neutral solution containing from 0.2 to 2 percent of BDDE by weight based on total solution weight (Solution C1). Optionally, BDDE was dissolved at room temperature in a portion of solution A to form an alkaline solution containing from 1 to 10 percent of BDDE by weight based on total solution weight (Solution C2). Solution C (C1 neutral or C2 alkaline) is then added to the solution B to provide an alkaline solution with a hydroxide concentration in the final solution in the range from 0.25 and 0.75M and with the desired ratio of HA and BDDE. The resulting alkaline solution consisting of HA, BDDE and NaOH is then thoroughly mixed at room temperature. The homogenous solution was then left to react at controlled temperature in the range between 20 and 50° C. for a period comprised from 30 min to 48 hours.

The comparative BDDE cross-linked hyaluronic acid (hydrogel) was then washed with acidic water solution (1M hydrochloric acid and PBS) from 48 to 120 hours to remove unreacted materials and by products, to neutralize alkaline catalyst and restore the pH of hydrogel to 6.5-7.4 by ion exchange and to reach the concentration of HA in the comparative BDDE cross-linked hyaluronic acid (hydrogel) from 1 to 50 mg/mL. To the washed comparative BDDE cross-linked hyaluronic acid thus obtained, the glycerol or alternatively the mannitol was added directly to the washed hydrogel.

The one or more local anesthetic agents as hydrochloride salt dry powder were gently dissolved at room temperature (25° C.) in a portion of phosphate buffered saline solution to form a local anesthetic solution containing from 1 to 20 percent of local anesthetic by weight based on total solution weight having acceptable physiological pH (Solution D). The solution D is then added and mixed to the washed BDDE cross-linked hyaluronic acid hydrogel further containing the glycerol or mannitol obtained in previous section to reach the desired final concentration of HA (from 1 to 50 mg/mL), for the glycerol or mannitol (from 1 to 50 mg/mL) and local anesthetic (LA) (from 0.1 to 10 mg/mL)

The comparative BDDE cross-linked hyaluronic acid (hydrogel) containing the free glycerol or mannitol and the local anesthetic was filled into syringes and steam sterilized in autoclave following the pharmacopeia accepted procedures reported in the EN ISO 17665-1, Sterilization of health care products—Moist heat Part 1: requirements for the development, validation, and routine control of a sterilization process for medical device (e.g. 15 min at 121° C.).

The comparative BDDE cross-linked hyaluronic acid (hydrogel) containing the free glycerol or mannitol and the local anesthetic could be optionally dehydrated under vacuum at 30° C. or lyophilized (freeze-dried) and stored for following use or analysis.

2.1.3.2. Characterization of the Comparative Conjugate of BDDE Crosslinked Hyaluronic Acid, Local Anesthetic and Free Glycerol or Mannitol The chemical composition of the comparative BDDE cross-linked hyaluronic acid conjugate containing local anesthetic are disclosed in Tables 8-15.

TABLE 8

NON-STERILIZED Comparative conjugate
BDDE cross-linked HA containing GLYCEROL and LIDOCAINE

| Comp. Ex. | Conc. HA[a] | Cross-linker | C.D. (%) | Conc. free Gly[b] | Free Gly MW range | pH | Conc LA[c] | % B | pKa[s] |
|---|---|---|---|---|---|---|---|---|---|
| 71 | 25 | BDDE | 0.3419 | 25 | 74 ÷ 166 | 7.4 | 3 | 23.82 | 7.90 |
| 72 | 25 | BDDE | 0.3419 | 5 | 74 ÷ 166 | 7.4 | 3 | 23.81 | 7.91 |
| 73 | 15 | BDDE | 0.2008 | 0.5 | 74 ÷ 166 | 7.4 | 3 | 23.69 | 7.91 |
| 74 | 20 | BDDE | 0.2655 | 0.5 | 74 ÷ 166 | 7.4 | 3 | 23.54 | 7.91 |
| 75 | 25 | BDDE | 0.3419 | 0.5 | 74 ÷ 166 | 7.4 | 3 | 24.09 | 7.90 |
| 76 | 30 | BDDE | 0.4522 | 0.5 | 74 ÷ 166 | 7.4 | 3 | 24.47 | 7.89 |
| 77 | 25 | BDDE | 0.2374 | 0.5 | 74 ÷ 166 | 7.4 | 1 | 25.06 | 7.88 |
| 78 | 25 | BDDE | 0.3389 | 0.5 | 74 ÷ 166 | 7.4 | 9 | 21.90 | 7.95 |
| 79 | 25 | BDDE | 0.3389 | 0.5 | 74 ÷ 166 | 7.2 | 3 | 16.33 | 7.91 |
| 80 | 25 | BDDE | 0.3389 | 0.5 | 74 ÷ 166 | 7.0 | 3 | 11.21 | 7.90 |

TABLE 9

STERILIZED Comparative conjugate
BDDE cross-linked HA containing GLYCEROL and LIDOCAINE

| Comp. Ex. | Conc. HA[a] | Cross-linker | C.D. (%) | Conc. free Gly[b] | Free Gly MW range | pH | Conc LA[c] | % B | pKa[s] |
|---|---|---|---|---|---|---|---|---|---|
| 81 | 25 | BDDE | 0.2786 | 25 | 74 ÷ 166 | 7.4 | 3 | 24.12 | 7.90 |
| 82 | 25 | BDDE | 0.2786 | 5 | 74 ÷ 166 | 7.4 | 3 | 24.26 | 7.90 |
| 83 | 15 | BDDE | 0.1615 | 0.5 | 74 ÷ 166 | 7.4 | 3 | 24.02 | 7.90 |
| 84 | 20 | BDDE | 0.2155 | 0.5 | 74 ÷ 166 | 7.4 | 3 | 24.22 | 7.90 |
| 85 | 25 | BDDE | 0.2786 | 0.5 | 74 ÷ 166 | 7.4 | 3 | 24.06 | 7.90 |
| 86 | 30 | BDDE | 0.3724 | 0.5 | 74 ÷ 166 | 7.4 | 3 | 24.53 | 7.89 |
| 87 | 25 | BDDE | 0.1989 | 0.5 | 74 ÷ 166 | 7.4 | 1 | 25.28 | 7.87 |
| 88 | 25 | BDDE | 0.2701 | 0.5 | 74 ÷ 166 | 7.4 | 9 | 22.18 | 7.95 |
| 89 | 25 | BDDE | 0.2701 | 0.5 | 74 ÷ 166 | 7.2 | 3 | 16.28 | 7.91 |
| 90 | 25 | BDDE | 0.2701 | 0.5 | 74 ÷ 166 | 7.0 | 3 | 11.03 | 7.91 |

TABLE 10

NON-STERILIZED Comparative conjugate
BDDE cross-linked HA containing GLYCEROL and MEPIVACAINE

| Comp. Ex. | Conc. HA[a] | Cross-linker | C.D. (%) | Conc. free Gly[b] | Free Gly MW range | pH | Conc LA[c] | % B | pKa[s] |
|---|---|---|---|---|---|---|---|---|---|
| 91 | 25 | BDDE | 0.3419 | 25 | 74 ÷ 166 | 7.4 | 3 | 28.42 | 7.80 |
| 92 | 25 | BDDE | 0.3419 | 5 | 74 ÷ 166 | 7.4 | 3 | 27.34 | 7.82 |
| 93 | 15 | BDDE | 0.2008 | 0.5 | 74 ÷ 166 | 7.4 | 3 | 28.18 | 7.81 |
| 94 | 20 | BDDE | 0.2655 | 0.5 | 74 ÷ 166 | 7.4 | 3 | 27.65 | 7.82 |
| 95 | 25 | BDDE | 0.3419 | 0.5 | 74 ÷ 166 | 7.4 | 3 | 28.48 | 7.80 |
| 96 | 30 | BDDE | 0.4522 | 0.5 | 74 ÷ 166 | 7.4 | 3 | 28.46 | 7.80 |
| 97 | 25 | BDDE | 0.2374 | 0.5 | 74 ÷ 166 | 7.4 | 1 | 29.41 | 7.78 |
| 98 | 25 | BDDE | 0.3389 | 0.5 | 74 ÷ 166 | 7.4 | 9 | 26.89 | 7.83 |
| 99 | 25 | BDDE | 0.3389 | 0.5 | 74 ÷ 166 | 7.2 | 3 | 19.94 | 7.80 |
| 100 | 25 | BDDE | 0.3389 | 0.5 | 74 ÷ 166 | 7.0 | 3 | 13.28 | 7.81 |

TABLE 11

STERILIZED Comparative conjugate
BDDE cross-linked HA containing GLYCEROL and MEPIVACAINE

| Comp. Ex. | Conc. HA[a] | Cross-linker | C.D. (%) | Conc. free Gly[b] | Free Gly MW range | pH | Conc LA[c] | % B | pKa[s] |
|---|---|---|---|---|---|---|---|---|---|
| 101 | 25 | BDDE | 0.2786 | 25 | 74 ÷ 166 | 7.4 | 3 | 28.76 | 7.79 |
| 102 | 25 | BDDE | 0.2786 | 5 | 74 ÷ 166 | 7.4 | 3 | 27.83 | 7.81 |
| 103 | 15 | BDDE | 0.1615 | 0.5 | 74 ÷ 166 | 7.4 | 3 | 28.55 | 7.80 |
| 104 | 20 | BDDE | 0.2155 | 0.5 | 74 ÷ 166 | 7.4 | 3 | 28.41 | 7.80 |
| 105 | 25 | BDDE | 0.2786 | 0.5 | 74 ÷ 166 | 7.4 | 3 | 28.45 | 7.80 |
| 106 | 30 | BDDE | 0.3724 | 0.5 | 74 ÷ 166 | 7.4 | 3 | 28.53 | 7.80 |
| 107 | 25 | BDDE | 0.1989 | 0.5 | 74 ÷ 166 | 7.4 | 1 | 29.65 | 7.78 |
| 108 | 25 | BDDE | 0.2701 | 0.5 | 74 ÷ 166 | 7.4 | 9 | 27.22 | 7.83 |
| 109 | 25 | BDDE | 0.2701 | 0.5 | 74 ÷ 166 | 7.2 | 3 | 19.89 | 7.81 |
| 110 | 25 | BDDE | 0.2701 | 0.5 | 74 ÷ 166 | 7.0 | 3 | 13.07 | 7.82 |

TABLE 12

NON-STERILIZED Comparative conjugate
BDDE cross-linked HA containing GLYCEROL and ARTICAINE

| Comp. Ex. | Conc. HA[a] | Cross-linker | C.D. (%) | Conc. free Gly[b] | Free Gly MW range | PH | Conc LA[c] | % B | pKa[s] |
|---|---|---|---|---|---|---|---|---|---|
| 111 | 25 | BDDE | 0.3419 | 25 | 74 ÷ 166 | 7.4 | 3 | 37.94 | 7.61 |
| 112 | 25 | BDDE | 0.3419 | 5 | 74 ÷ 166 | 7.4 | 3 | 38.43 | 7.60 |
| 113 | 15 | BDDE | 0.2008 | 0.5 | 74 ÷ 166 | 7.4 | 3 | 38.02 | 7.61 |
| 114 | 20 | BDDE | 0.2655 | 0.5 | 74 ÷ 166 | 7.4 | 3 | 37.62 | 7.62 |
| 115 | 25 | BDDE | 0.3419 | 0.5 | 74 ÷ 166 | 7.4 | 3 | 38.68 | 7.60 |
| 116 | 30 | BDDE | 0.4522 | 0.5 | 74 ÷ 166 | 7.4 | 3 | 38.60 | 7.60 |
| 117 | 25 | BDDE | 0.2374 | 0.5 | 74 ÷ 166 | 7.4 | 1 | 38.42 | 7.60 |
| 118 | 25 | BDDE | 0.3389 | 0.5 | 74 ÷ 166 | 7.4 | 9 | 37.66 | 7.62 |
| 119 | 25 | BDDE | 0.3389 | 0.5 | 74 ÷ 166 | 7.2 | 3 | 28.28 | 7.60 |
| 120 | 25 | BDDE | 0.3389 | 0.5 | 74 ÷ 166 | 7.0 | 3 | 20.04 | 7.60 |

TABLE 13

STERILIZED Comparative conjugate
BDDE cross-linked HA containing GLYCEROL and ARTICAINE

| Comp. Ex. | Conc. HA[a] | Cross-linker | C.D. (%) | Conc. free Gly[b] | Free Gly MW range | pH | Conc LA[c] | % B | pKa[s] |
|---|---|---|---|---|---|---|---|---|---|
| 121 | 25 | BDDE | 0.2786 | 25 | 74 ÷ 166 | 7.4 | 3 | 38.33 | 7.61 |
| 122 | 25 | BDDE | 0.2786 | 5 | 74 ÷ 166 | 7.4 | 3 | 39.02 | 7.59 |
| 123 | 15 | BDDE | 0.1615 | 0.5 | 74 ÷ 166 | 7.4 | 3 | 38.45 | 7.60 |
| 124 | 20 | BDDE | 0.2155 | 0.5 | 74 ÷ 166 | 7.4 | 3 | 38.51 | 7.60 |
| 125 | 25 | BDDE | 0.2786 | 0.5 | 74 ÷ 166 | 7.4 | 3 | 38.64 | 7.60 |
| 126 | 30 | BDDE | 0.3724 | 0.5 | 74 ÷ 166 | 7.4 | 3 | 38.68 | 7.60 |
| 127 | 25 | BDDE | 0.1989 | 0.5 | 74 ÷ 166 | 7.4 | 1 | 38.69 | 7.60 |
| 128 | 25 | BDDE | 0.2701 | 0.5 | 74 ÷ 166 | 7.4 | 9 | 38.05 | 7.61 |
| 129 | 25 | BDDE | 0.2701 | 0.5 | 74 ÷ 166 | 7.2 | 3 | 28.21 | 7.61 |
| 130 | 25 | BDDE | 0.2701 | 0.5 | 74 ÷ 166 | 7.0 | 3 | 19.75 | 7.61 |

TABLE 14

NON-STERILIZED Comparative conjugate
BDDE cross-linked HA containing MANNITOL and LIDOCAINE

| Comp. Ex. | Conc. HA[a] | Cross-linker | C.D. (%) | Conc. free Mann[d] | Free Mann MW range | pH | Conc LA[c] | % B | pKa[s] |
|---|---|---|---|---|---|---|---|---|---|
| 131 | 25 | BDDE | 0.3419 | 25 | 146 ÷ 182 | 7.4 | 3 | 24.05 | 7.90 |
| 132 | 25 | BDDE | 0.3419 | 5 | 146 ÷ 182 | 7.4 | 3 | 24.10 | 7.90 |
| 133 | 15 | BDDE | 0.2008 | 0.5 | 146 ÷ 182 | 7.4 | 3 | 24.06 | 7.90 |
| 134 | 20 | BDDE | 0.2655 | 0.5 | 146 ÷ 182 | 7.4 | 3 | 24.16 | 7.90 |
| 135 | 25 | BDDE | 0.3419 | 0.5 | 146 ÷ 182 | 7.4 | 3 | 24.00 | 7.90 |
| 136 | 30 | BDDE | 0.4522 | 0.5 | 146 ÷ 182 | 7.4 | 3 | 24.75 | 7.88 |
| 137 | 25 | BDDE | 0.2374 | 0.5 | 146 ÷ 182 | 7.4 | 1 | 24.89 | 7.88 |
| 138 | 25 | BDDE | 0.3389 | 0.5 | 146 ÷ 182 | 7.4 | 9 | 24.01 | 7.90 |

TABLE 14-continued

NON-STERILIZED Comparative conjugate
BDDE cross-linked HA containing MANNITOL and LIDOCAINE

| Comp. Ex. | Conc. HA[a] | Cross-linker | C.D. (%) | Conc. free Mann[d] | Free Mann MW range | pH | Conc LA[c] | % B | pKa$^s$ |
|---|---|---|---|---|---|---|---|---|---|
| 139 | 25 | BDDE | 0.3389 | 0.5 | 146 ÷ 182 | 7.2 | 3 | 16.46 | 7.91 |
| 140 | 25 | BDDE | 0.3389 | 0.5 | 146 ÷ 182 | 7.0 | 3 | 10.66 | 7.92 |

TABLE 15

STERILIZED Comparative conjugate
BDDE cross-linked HA containing MANNITOL and LIDOCAINE

| Comp. Ex. | Conc. HA[a] | Cross-linker | C.D. (%) | Conc. free Mann[d] | Free Mann MW range | pH | Conc LA[c] | % B | pKa$^s$ |
|---|---|---|---|---|---|---|---|---|---|
| 141 | 25 | BDDE | 0.2786 | 25 | 146 ÷ 182 | 7.4 | 3 | 24.05 | 7.90 |
| 142 | 25 | BDDE | 0.2786 | 5 | 146 ÷ 182 | 7.4 | 3 | 24.10 | 7.90 |
| 143 | 15 | BDDE | 0.1615 | 0.5 | 146 ÷ 182 | 7.4 | 3 | 24.06 | 7.90 |
| 144 | 20 | BDDE | 0.2155 | 0.5 | 146 ÷ 182 | 7.4 | 3 | 24.16 | 7.90 |
| 145 | 25 | BDDE | 0.2786 | 0.5 | 146 ÷ 182 | 7.4 | 3 | 24.00 | 7.90 |
| 146 | 30 | BDDE | 0.3724 | 0.5 | 146 ÷ 182 | 7.4 | 3 | 24.75 | 7.88 |
| 147 | 25 | BDDE | 0.1989 | 0.5 | 146 ÷ 182 | 7.4 | 1 | 24.89 | 7.88 |
| 148 | 25 | BDDE | 0.2701 | 0.5 | 146 ÷ 182 | 7.4 | 9 | 24.01 | 7.90 |
| 149 | 25 | BDDE | 0.2701 | 0.5 | 146 ÷ 182 | 7.2 | 3 | 16.46 | 7.91 |
| 150 | 25 | BDDE | 0.2701 | 0.5 | 146 ÷ 182 | 7.0 | 3 | 10.66 | 7.92 |

(a) concentration of HA in the comparative BDDE cross-linked HA expressed as mg/mL (b) concentration of free glycerol in the comparative BDDE cross-linked HA expressed as mg/mL, and its chemical structure were measured by SEC/UV/MS.

(c) concentration of local anesthetic (LA) in the comparative BDDE cross-linked HA expressed as mg/mL, measured by GC/MS and by SEC/UV/MS.

(d) concentration of free Mannitol in the comparative BDDE cross-linked HA expressed as mg/mL (measured by SEC/UV/MS).

To sum up, the comparative BDDE cross-linked HA conjugate falling outside of the scope of the present invention were obtained using different amount of BDDE. The comparative BDDE cross-linked HA conjugate ranged from 15 to 30 mg/mL of crosslinked hyaluronic acid concentration, which means showing different crosslinking degrees disclosed in corresponding tables above. As it is mentioned above, the comparative BDDE cross-linked HA conjugate contains free polyols (glycerol or mannitol) in the range of 0.5 to 25 mg/mL.

Further, the comparative BDDE cross-linked HA conjugate contains a percentage of neutral form B of local anesthetic comparable to the predicted thermodynamic value from Henderson-Hasselbalch equation, e.g. at pH 7.4. Therefore, the pKa$^S$ experimentally calculated for the local anesthetic at a fixed pH value calculated by means of the Henderson-Hasselbalch equation, using experimental concentrations of B and BH$^+$ are not statistically different from the thermodynamic pKa.

2.1.4. Analytical Activity 2.1.4.1. Sample Solution Preparation and Data Elaboration The quantitative analysis was conducted in triplicate on three different batches of each product, the results were reported as mean value ±standard deviation. An aliquot of the product to be analysed was diluted 50 times with water obtaining the "Sample Solution".

For the chromatographic analytical techniques (GC/MS and SEC/UV/MS), the compounds were considered only if the peak area in the sample solutions was 3 times greater than the signal/noise ratio, imposed as parameter in the instrument software. The quantification was performed as difference between the peak area in the sample solution and the peak area of the blank solution.

For the techniques using the mass detector, the concentration of each compound was calculated by the abundance of its mass signals from the Total Ion Chromatogram (TIC), for the techniques using the UV-Vis detector, the concentration of each compound was calculated using the equation derived from the calibration curve obtained by several concentration of the pure compound.

In order to assess that the GC/MS and SEC/UV/MS analytical methods are suitable for the detection of the compounds from the sample, reference standards were chosen among the most common local anesthetic agents and further analysed.

2.1.4.2. Quantitative Method for the Measurement of the Semi-Volatile Compounds Using GC/MS Chromatographic Instrument for the Neutral Fraction of Local Anesthetics.

Sample Preparation

An aliquot of the "Sample Solution" was extracted 1:1 with $CH_2Cl_2$ and organic phase was analysed.

Data Analysis

Chromatograms obtained from sample solutions analysis were evaluated and all the peaks detected with signal/noise above 3 were reported and an identification was attempted using the MS library (Wiley Registry 11$^{th}$ Edition/NIST 2017 Mass Spectral Library, available on the website https://webbook.nist.gov/chemistry/ on Jun. 28, 2021). A Phenanthrene-d10 solution (QL=1 µg/mL) was used as internal standard for the quantification of the compounds.

Results

The quantitative results of analytical method of the comparative BDDE cross-linked hyaluronic acid, and the PPE crosslinked hyaluronic acid of the present invention were summarized in Tables disclosed above. Concentration of neutral form of local anesthetic B was combined with concentration of ionized form BH$^+$ found using SEC/UV/

MS in order to obtain the percentage of B over the total LA (B+BH$^+$), the percentage of B and experimental pKa$^S$ reported in tables disclosed above.

2.1.4.3 Quantitative Method for the Measurement of the Non-Volatile Compounds Using SEC/UV/MS Chromatographic Instrument for the Total Amount of Local Anesthetics and Free Glycerol, Polyglycerol and Mannitol Fragments and their Chemical Structure.

Sample Preparation

An aliquot of the "Sample Solution" was analysed by SEC/UV/MS without further treatments.

Data Analysis

Chromatograms obtained from sample solutions analysis were evaluated and all the peaks detected with signal/noise above 3 were reported and an identification was attempted using the MS library (Wiley Registry 11th Edition/NIST 2017 Mass Spectral Library). A Reserpine solution (QL=1 µg/mL) was used as internal standard for the quantification of the compounds.

Chemical structure of free glycerol, polyglycerols and mannitol fragments were evaluated using mass spectroscopy as detector of the SEC, mass spectra of all detected peaks were compared with references using the MS library (Wiley Registry 11th Edition/NIST 2017 Mass Spectral Library).

Results

The quantitative results of analytical method of the comparative BDDE crosslinked hyaluronic acid, and the PPE crosslinked hyaluronic acid of the present invention are summarized in Tables above.

Concentration of free polyglycerols are expressed in mg/mL, concentration of ionized form of local anesthetic BH$^+$ was combined with concentration of neutral form B found using GC/MS in order to obtain the percentage of B over the total LA (B+BH$^+$), the percentage of B and experimental pKa$^S$ reported in tables above.

2.1.4.4 Quantitative Method for the Determination of Neutral Fraction and Total Amount of Local Anesthetics Using UV-Vis Spectrophotometer for Kinetic Release.

Sample Preparation

An aliquot of the "Sample Solution" was analysed by UV-Vis spectrophotometer without further treatments for the determination of the total amount of Local Anesthetics (B+BH$^+$).

An aliquot of the "Sample Solution" was extracted 1:1 with $CH_2Cl_2$ and organic phase was analysed by UV-Vis spectrophotometer for the determination of the neutral fraction of Local Anesthetics (B).

Data Analysis

The concentration of each compound was calculated using the equation derived from the calibration curve obtained by several concentration of the pure compound.

2.1.5 Kinetic Release of the Local Anesthetic

The kinetic release of the local anesthetic agent from PPE crosslinked hyaluronic acid of the present invention, from the comparative BDDE crosslinked hyaluronic acid and from water solution (as control) were summarized below.

Samples:

As control, a solution containing the local anesthetic was prepared dissolving at room temperature powder local anesthetic in phosphate buffered saline solution (PBS) to form a local anesthetic phosphate buffered saline containing from 0.1 to 10 percent of the local anesthetic by weight based on total solution weight, the pH of the solution was adjusted to 7.4 using NaOH 0.2M and HCl 0.2M.

The non-sterilized and sterilized PPE hyaluronic acid (Ex. 3 and Ex. 18) and the comparative non-sterilized and sterilized BDDE crosslinked hyaluronic acid (Comp. Ex. 85 and Comp. Ex. 75) containing the local anesthetic were used without any further treatment.

Method:

5 ml of each sample (control, PPE and comparative BDDE crosslinked HA) containing the local anesthetic was put in a SpectraPor® Float-A-Lyzer Dialysis Device of 5 mL size and 20 kD of MWCO and closed. The dialysis tube was immersed in a glass bottle with a screw cap containing 245 mL of phosphate buffered saline solution (dilution 50 times). The solution was gently stirred in a thermostatic bath at 37° C. until the total anesthetic was totally released and the local anesthetic concentration was in equilibrium between the sample and the external PBS solution.

At fixed period of time a sample solution was removed from the external phosphate buffered saline solution and analysed for the total amount of the total local anesthetic release using UV-Vis Spectrophotometer.

The concentration of the released local anesthetic was calculated using the equation derived from the calibration curve obtained by several concentration of the pure local anesthetic. The calibration curve with local anesthetic standard solutions (from 3.0 µg/ml to 45 µg/ml) was obtained by an UV-Vis spectrophotometer using a quartz cell of 1 cm optical path. Absorption spectra were acquired in the range 200÷300 nm.

After 120 hours, an aliquot of the external phosphate buffered saline solution was extracted 1:1 with $CH_2Cl_2$ and the organic phase was analysed using GC/MS chromatographic instrument described in section 2.1.4.2. and an aliquot of the external phosphate buffered saline solution was analysed by SEC/UV/MS without further treatments using SEC/UV/MS chromatographic instrument described in section 2.1.4.3.

Results:

The percentage of the total amount of 3 mg/mL of the local anesthetic lidocaine from the buffered saline solution control, the non-sterilized and sterilized PPE (Examples 3 and 18) and the comparative non-sterilized and sterilized BDDE (Comparatives Ex. 85 and Ex. 75) crosslinked hyaluronic acid having comparable crosslinking degree.

Percentage of the total amount of lidocaine after 1, 2, 48 and 120 hours of release in water from the PBS, and non-sterilized PPE (Example 3) and the comparative non-sterilized BDDE (Comp. Ex. 85) crosslinked hyaluronic acid is summarised in Table 16 below:

TABLE 16

KINETIC RELEASE OF LIDOCAINE FROM NON-STERILIZED CROSSLINKED HYALURONIC ACID

| TIME (h) | From PBS (%) (CONTROL) | From BDDE/HA (%) Comp. Ex. 85 | From PPE/HA (%) Ex. 3 |
|---|---|---|---|
| 1 | 51.4 ± 0.43 | 1.94 ± 0.87 | 3.59 ± 2.12 |
| 2 | 65.37 ± 1.56 | 3.81 ± 2.10 | 6.95 ± 1.89 |
| 48 | 97.56 ± 2.63 | 48.29 ± 2.67 | 65.19 ± 2.42 |
| 120 | 98.22 ± 2.69 | 81.77 ± 3.99 | 89.83 ± 2.25 |

Percentage of the total amount of lidocaine after 1,2, 48 and 120 hours of release in water from the PBS, from sterilized PPE (Example 18) and comparative sterilized BDDE (Comp. Ex. 75) crosslinked hyaluronic acid is summarised in Table 17 below:

TABLE 17

KINETIC RELEASE OF LIDOCAINE FROM STERILIZED HYALURONIC ACID

| TIME (h) | From PBS (%) | From BDDE/HA (%) Comp. Ex. 75 | From PPE/HA (%) Ex. 18 |
|---|---|---|---|
| 1 | 52.99 ± 1.32 | 2.35 ± 0.43 | 4.23 ± 0.34 |
| 2 | 69.53 ± 1.68 | 4.62 ± 1.56 | 8.15 ± 1.14 |
| 48 | 97.44 ± 2.40 | 55.97 ± 2.63 | 73.25 ± 3.62 |
| 120 | 98.37 ± 2.40 | 83.64 ± 2.85 | 92.56 ± 2.85 |

Furthermore, the distribution of neutral form B over total amount of lidocaine (B+BH$^+$) after 120 hours of release in phosphate buffered saline solution (totally released) from the non-sterilized and sterilized PPE crosslinked and comparative BDDE crosslinked hyaluronic acid is disclosed in table below:

TABLE 18

| Lidocaine released after 120 h | B (%) | pKa$^S$ |
|---|---|---|
| From PBS non-sterilized (CONTROL) | 23.92 | 7.90 |
| From PBS sterilized (CONTROL) | 24.01 | 7.90 |
| From non-sterilized BDDE/HA (Comp. Ex. 75) | 24.45 | 7.89 |
| From sterilized BDDE/HA (Comp. Ex. 85) | 24.06 | 7.90 |
| From non-sterilized PPE/HA (Ex. 3) | 44.90 | 7.49 |
| From sterilized PPE/HA (Ex. 18) | 48.67 | 7.45 |

Again, the distribution of neutral form B over total amount of lidocaine (B+BH$^+$) after 120 hours of release in phosphate buffered saline solution (totally released) showed that from the control (PBS) and from the non-sterilized and sterilized comparative BDDE crosslinked HA, the neutral form B of the released lidocaine is very similar to the predicted thermodynamic value from Henderson-Hasselbalch equation and consequently, the apparent pKa$^S$ is not statistically different from the thermodynamic pKa (pKa$^T$=7.9). Instead, from the non-sterilized and sterilized PPE crosslinked HA of the present invention, the neutral form B of the released lidocaine is much higher than the predicted thermodynamic value from Henderson-Hasselbalch equation and consequently, the apparent pKa$^S$ is much lower than the thermodynamic pKa, confirming the results reported in tables above.

Thus, regarding all the results mentioned above, it can be concluded that the onset of local anesthetics depends on their pKa, at the physiological pH value of 7.4, the local anesthetic having the shortest onset is that whose pKa is the closest to 7.4, since its liposoluble and bioavailable form will be that which will penetrate the epineurium and the neuronal membrane, thereafter, allowing the active ingredient molecule to be more rapidly available for blocking the sodium channels. In other words, the onset depends on the ratio B/BH$^+$ (or % B) at the moment of the injection and the rate of the conversion from BH$^+$ to B, that could be influenced in vivo by many factors. The ionization constant (pKa), specific for each anesthetic predicts the proportion of molecules that exists in each of these states. The pH of the anesthetic water solution and the pKa of the local anesthetic are therefore the most important factors influencing the onset of the local anesthetics.

Thus, as it is shown in the experimental data (cf. Tables 2-7), hydrogels Ex. 1, Ex.2 and Ex. 3 have the fastest onset of lidocaine at pH 7.24, pH 7.38 and 7.50, respectively. Meanwhile, the comparative hydrogels known in the state of the art (cf. Tables 8-15), the fastest onset is at pH 7.9 for lidocaine, 7.8 for mepivacaine and 7.6 for articaine, respectively. Therefore, all of the comparative hydrogels have the fastest onset at a pH above 7.4 that are not considered physiological for injectable hyaluronic acid hydrogels (6.9-7.4).

Results

The local anesthetic (Lidocaine-LA) was released from each tested sample to the external PBS solution at different ratio. As it was shown in Tables 16-17, the lidocaine solution in non-sterilized and sterilized PBS control shown the fastest release and 100% of the lidocaine was released within 120 hours. However, the lidocaine release from the non-sterilized and sterilized PPE crosslinked hyaluronic acid of the present invention were faster than the comparative non-sterilized and sterilized BDDE crosslinked hyaluronic acid, respectively. It is remarkable that the sterilized PPE crosslinked HA of the present invention has a slightly higher kinetic release of lidocaine than the non-sterilized PPE crosslinked HA (probably attributed to the lower crosslinking degree of the non-sterilized ones due to thermal degradation in the sterilization process).

Therefore, the above-experimental data demonstrated that the PPE crosslinked hyaluronic acid conjugate with local anaesthetics allows shorten the onset time of the local anesthetic and thus lengthen the duration of the anesthetic action; which means an in vivo rapid onset and efficacy of the local anesthetics.

CITATION LIST

1. He, Z., et al., "Ultrasonication-assisted rapid determination of epoxide values in polymer mixtures containing epoxy resin". Analytical Methods, 2014, vol. 6(12), pp. 4257-4261.

2. cf. Academic press Dictionary of Science and Technology, 1992, pp. 531;

3. A terminological Dictionary of the Pharmaceutical Sciences. 2007, pp. 190.

4. René. Levy et al. "Determination of thermodynamic dissociation constants of local anaesthetic amines: influence of ionic strength" J. Pharm. Pharmac., 1972, vol. 24, pp. 841-847

5. Wiley Registry 11th Edition/NIST 2017 Mass Spectral Library

6. S. C. De Smedt, et al. "Viscoelastic and transient network properties of hyaluronic acid as a function of the concentration," Biorheology, 1993. vol. 30(1), pp. 31-41).

For reasons of completeness, various aspects of the invention are set out in the following numbered clauses:

Clause 1. A composition comprising:

A) one or more crosslinked hyaluronic acids selected from the group consisting of one or more of crosslinked hyaluronic acids of formula (I);

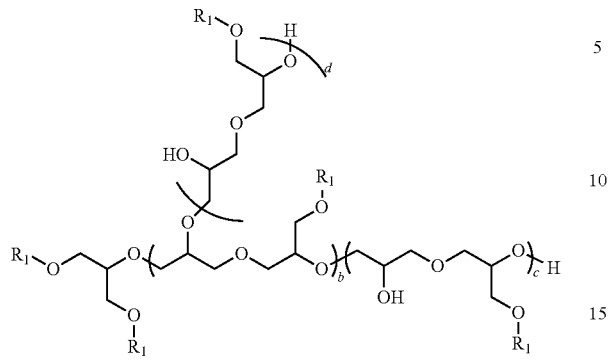
(I)
one or more of crosslinked hyaluronic acids of formula (II);
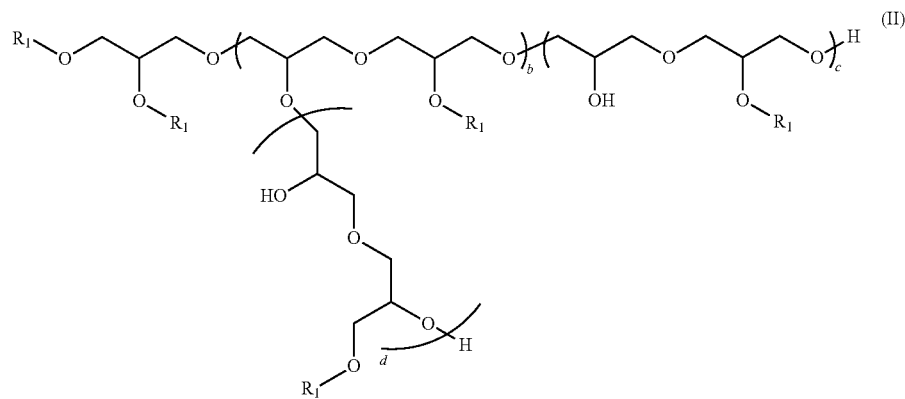
(II)
and a mixture of one or more crosslinked hyaluronic acids of formula (I) and one or more of crosslinked hyaluronic acids of formula (II);
B) one or more polyglycerols selected from the group consisting of one or more polyglycerols of formula (III);
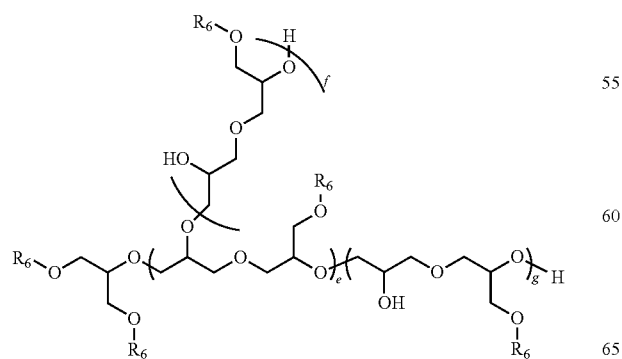
(III)

one or more polyglycerols of formula (IV);

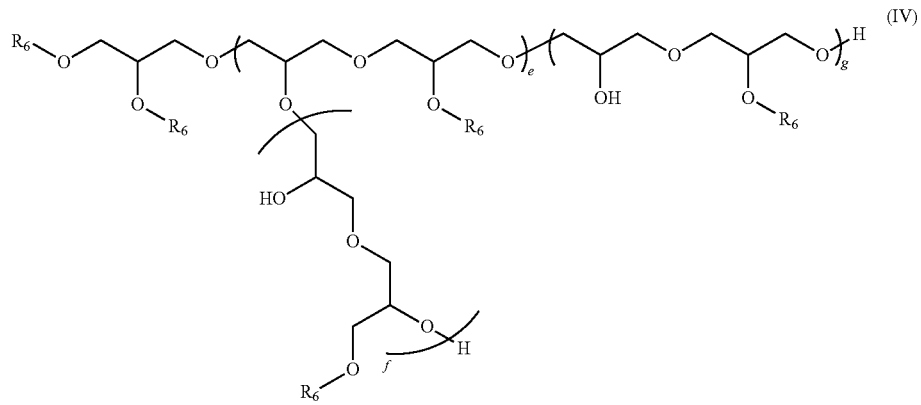

and a mixture of one or more polyglycerols of formula (III) and one or more polyglycerols of formula (IV);

C) one or more local anesthetic agents or a salt thereof; and

D) optionally, one or more acceptable excipients or carriers;

wherein:

each $R_1$ is independently selected from the group consisting of $R_2$, $R_3$, $R_4$ and $R_5$;

$R_2$

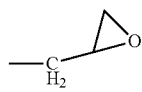

$R_3$ is

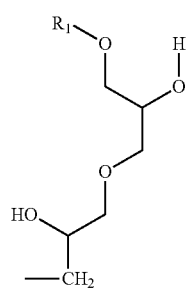

$R_4$ is

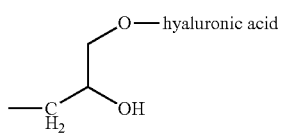

$R_5$ is

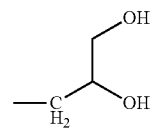

each $R_6$ is independently selected from the group consisting of $R_3$ and $R_5$;

b is an integer selected from the group consisting of 1 to 70;

c is an integer selected from the group consisting of 0 to 70;

d is an integer selected from the group consisting of 0 to 70;

e is an integer selected from the group consisting of 1 to 50;

f is an integer selected from the group consisting of 0 to 50;

g is an integer selected from the group consisting of 0 to 50;

the crosslinked hyaluronic acids of formula (I) or formula (II) have a crosslinking percentage from 0.030 to 0.900%; and the polyglycerols of formula (III) or formula (IV) have a weight average molecular weight ($M_w$) from 240 to 3.700 Da measured by size exclusion chromatography (SEC/UV/MS);

with the proviso that:

in the crosslinked hyaluronic acids of formula (I) or formula (II) at least one $R_1$ is $R_4$; and in the polyglycerols of formula (III) or formula (IV), if R1 is present, then $R_1$ is other than $R_4$.

Clause 2. The composition according to clause 1, wherein the crosslinked hyaluronic acid of formula (I), or of formula (II), or a mixture thereof, is obtained using PPE as crosslinker having a weight average molecular weight from 204 to 15000 Da measured by the method by size exclusion chromatography (SEC) and an epoxy equivalent weight from 100 to 7000 g/eq measured by ultrasonication-assisted rapid titration with HCl.

Clause 3. The composition according to any of the clauses 1 or 2, wherein comprising one or more local anesthetic agents or a salt thereof having a percentage of neutral form B of the local anesthetic determined by Gas Chromatography coupled with Mass detector from 40% to 160% higher than the predicted value calculated by the Henderson-Hasselbalch equation:

$$pH = pKa + \log\frac{[B]}{[BH^+]}$$

wherein:
pH is the $-\log([H^+])$,
pKa is the $-\log$ of the dissociation equilibrium constant of the weak acid;
[B] ([base]) is the concentration of the conjugate basic form of the local anesthetic; and
[BH+] ([acid]) is the conjugate acidic form of the local anesthetic.

Clause 4. The composition according to any of the clauses 1-3, wherein the molecular weight of the polyglycerols of formula (III) or formula (IV) is from 240 to 3700 Da measured by the method by size exclusion chromatography (SEC).

Clause 5. The composition according to any of the clauses 1-4, wherein the concentration of polyglycerols of formula (III) or formula (IV) or mixture thereof in the composition is from 0.45 to 25 mg/mL.

Clause 6. The composition according to any of the clauses 1-5, wherein the one or more polyglycerols of formula (III) or formula (IV) is selected from the group consisting of:

a compound of formula (1);

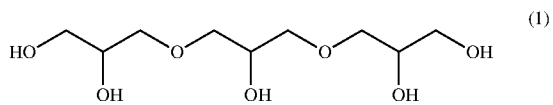 [SMILES: OCC(O)COCC(O)COCC(O)CO]

a compound of formula (2);

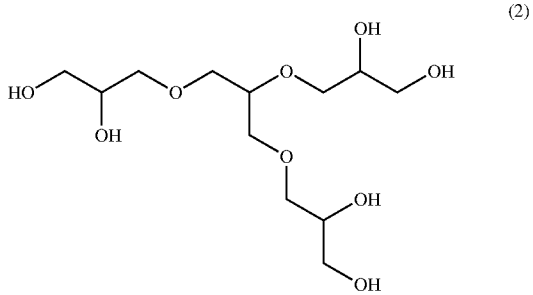 [SMILES: OCC(O)COCC(COCC(O)CO)OCC(O)CO]

a compound of formula (3);

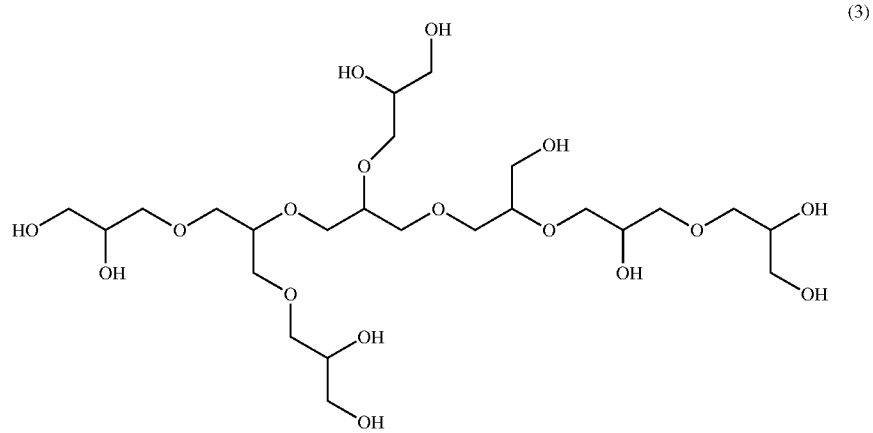 [SMILES: OCC(O)COCC(O)COC(CO)COCC(COC(COCC(O)CO)COCC(O)CO)OCC(O)CO]

a compound of formula (4);
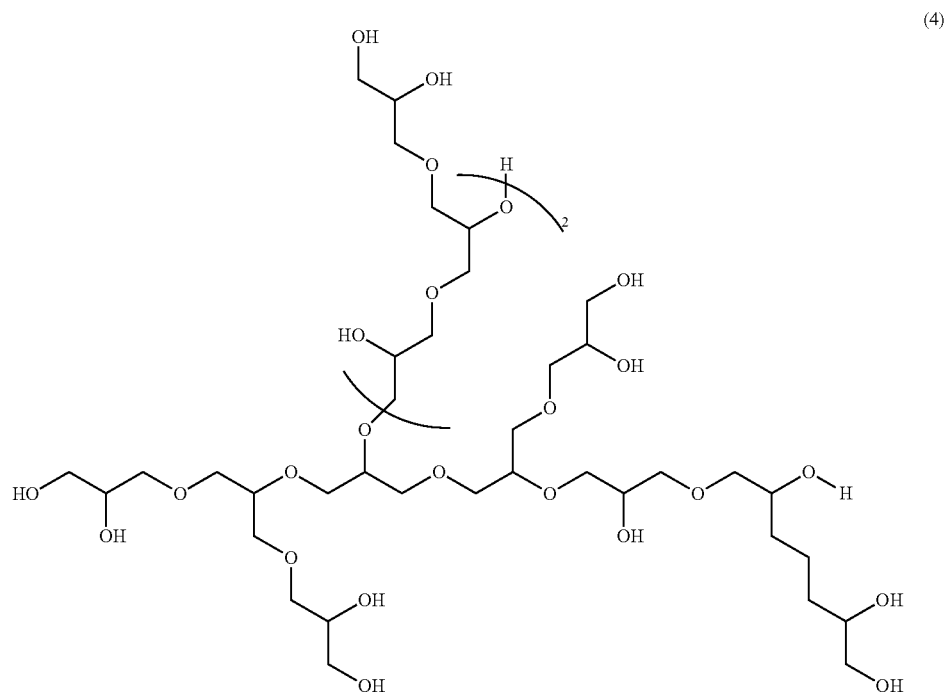
a compound of formula (5);
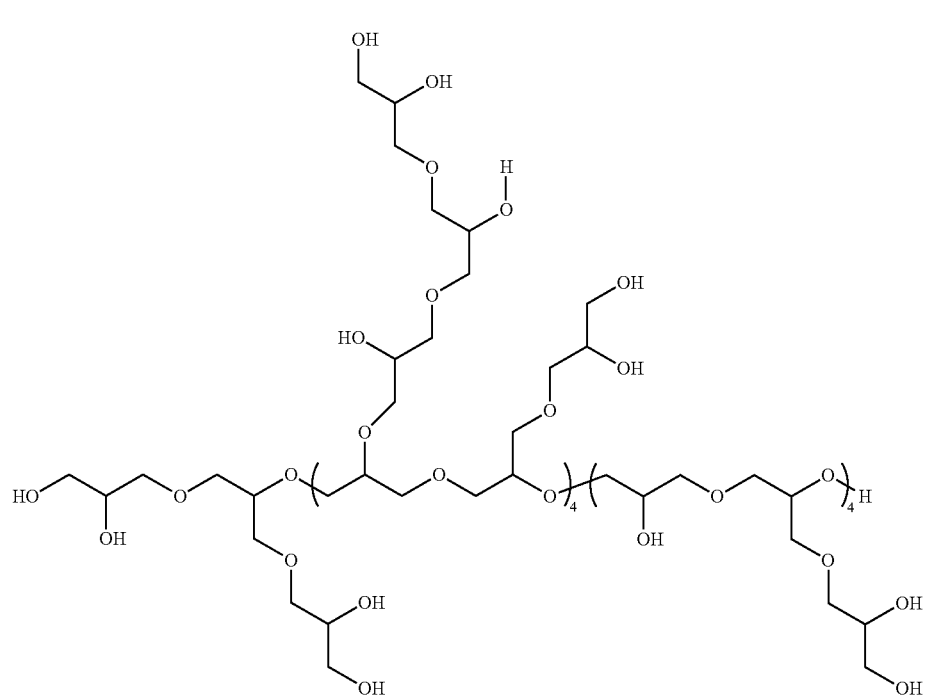

a compound of formula (6);

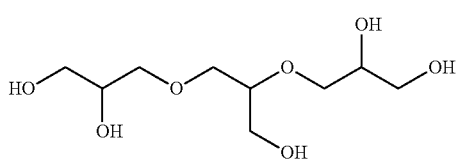

and a mixture thereof.

Clause 7. The composition according to any of the clauses 1-6, wherein the concentration of the hyaluronic acid in the crosslinked hyaluronic acid of formula (I) or formula (II) is from 1 to 50 mg/ml.

Clause 8. The composition according to any of the clauses 1-7, wherein the molecular weight of the hyaluronic acid of the crosslinked hyaluronic acid of formula (I) or formula (II) is from 100 to 3000 kDa measured by the method by size exclusion chromatography (SEC).

Clause 9. The composition according to any of the clauses 1-8, wherein the local anesthetic agent is selected from the group consisting of ambucaine, amolanone, amylocaine, articaine, benoxinate, benzocaine, betoxycaine, biphenamine, bupivacaine, butacaine, butamben, butanilicaine, butethamine, butoxycaine, chloroprocaine, cocaethylene, cocaine, cyclomethycaine, dibucaine, dimethyisoquin, dimethocaine, diperodon, dicyclomine, ecgonidine, ecgonine, etidocaine, beta-eucaine, euprocin, fenalcomine, farmocaine, fomocaine, hexylcaine, hydroxytetracaine, isobutyl p-aminobenzoate, leucinocaine mesylate, levoxadrol, lidocaine, mepivacaine, meprylcaine, metabutoxycaine, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and a mixture thereof.

Clause 10. The composition according to any of the clauses 1-9, wherein:
when the composition comprises (a) a crosslinked hyaluronic acid of formula (I), the composition is obtainable by a process which comprises:
i) crosslinking a hyaluronic acid with a compound of formula (V)

wherein:
each $R_1$ is independently selected from the group consisting of $R_2$ and $R_3$;
$R_2$ is

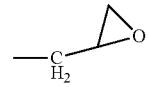

$R_3$ is

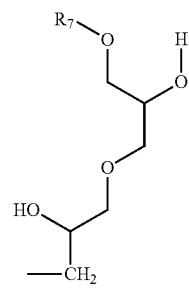

b is an integer selected from the group consisting of 1 to 70;
c is an integer selected from the group consisting of 0 to 70;
d is an integer selected from the group consisting of 0 to 70;
(ii) contacting the mixture obtained in step (i) comprising (A) one or more crosslinked hyaluronic acids of formula (I) and (B) one or more polyglycerols of formula (III) or formula (IV) with the one or more anesthetic agents (C);
(iii) optionally, contacting the mixture obtained in step (ii) with the one or more excipients or carriers (D); and
(iv) optionally, sterilizing the mixture obtained in step (iii);
or alternatively,
when the composition comprises (a) a crosslinked hyaluronic acid of formula (II), then the composition is obtainable by a process which comprises:
i') crosslinking a hyaluronic acid with a compound of formula (VI)

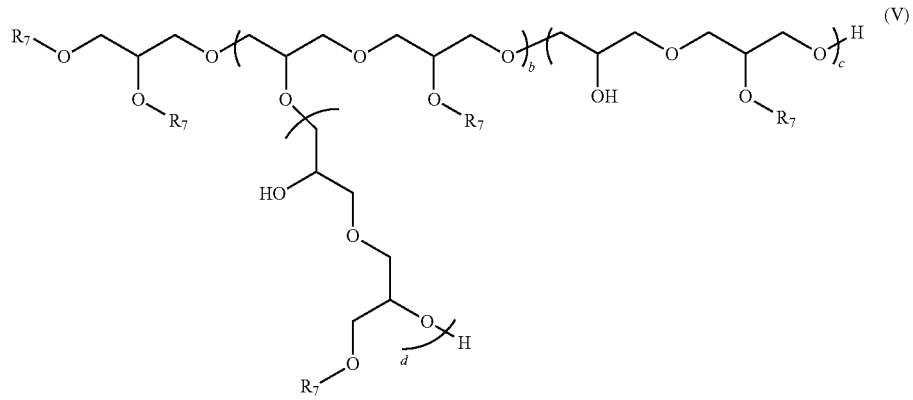

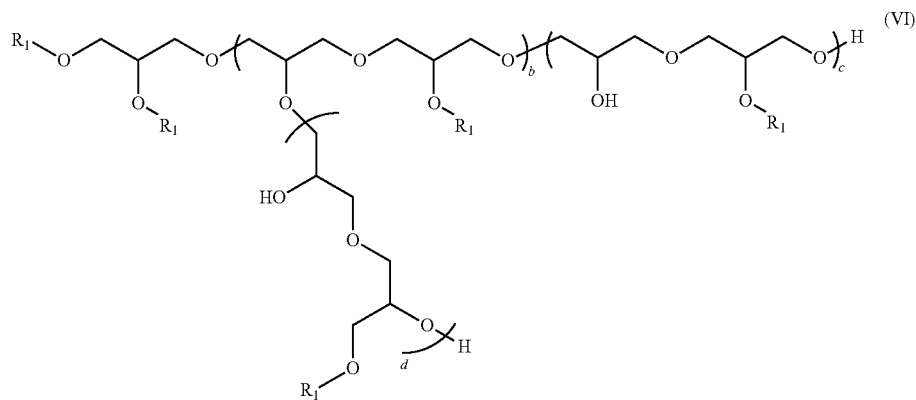

wherein:
each $R_1$ is independently selected from the group consisting of $R_2$ and $R_3$;
$R_2$ is

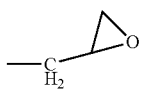

$R_3$ is

—CH$_2$ b is an integer selected from the group consisting of 1 to 70;
c is an integer selected from the group consisting of 0 to 70;
d is an integer selected from the group consisting of 0 to 70;

(ii') contacting the mixture obtained in step (i') comprising (A) one or more crosslinked hyaluronic acids of formula (II) and (B) one or more polyglycerols of formula (III) or formula (IV) with the one or more anesthetic agents (C);

(iii') optionally, contacting the mixture obtained in step (II') with the one or more excipients or carriers (D); and (iv') optionally, sterilizing the mixture obtained in step (iii');

or alternatively, when the composition comprises (a) a mixture of a crosslinked hyaluronic acid of formula (I) and of formula (II); then the composition is obtainable by a process which comprises:

I") crosslinking a hyaluronic acid with a mixture comprising the compound of formula (V)

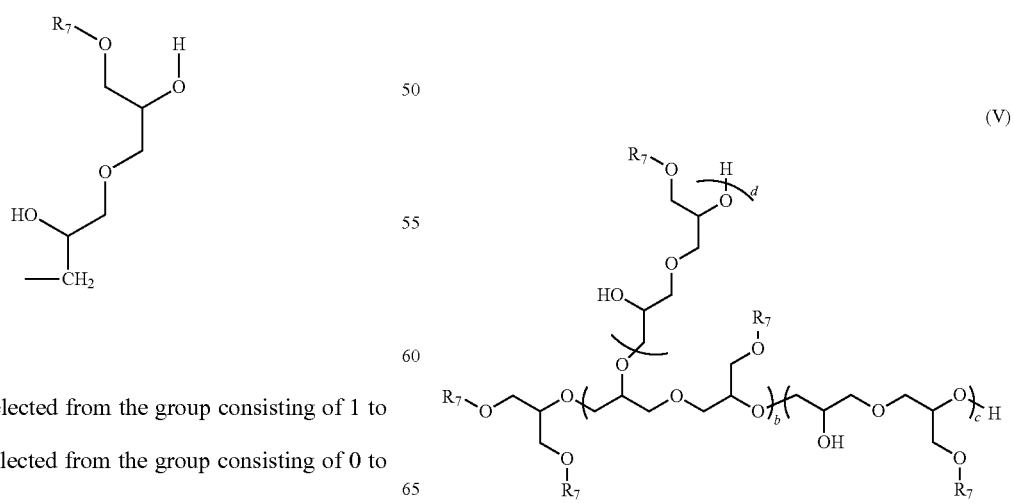

and of formula (VI)

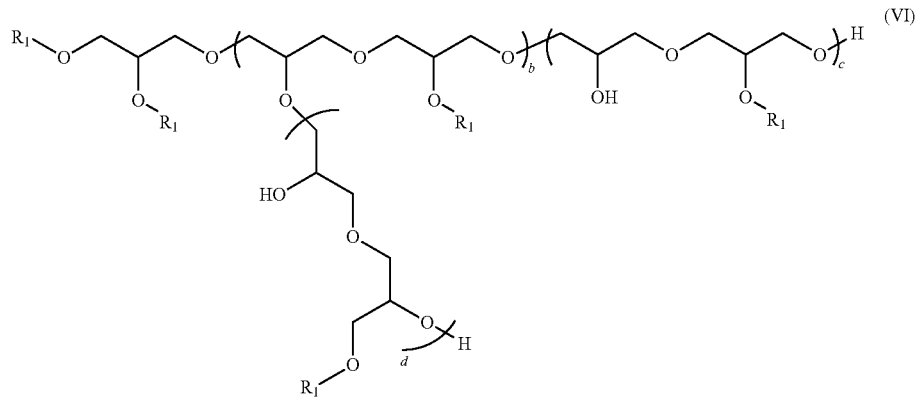

wherein:
each $R_1$ is independently selected from the group consisting of $R_2$ and $R_3$;
$R_2$ is

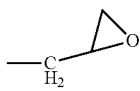

$R_3$ is

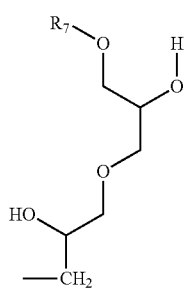

b is an integer selected from the group consisting of 1 to 70;
c is an integer selected from the group consisting of 0 to 70;
d is an integer selected from the group consisting of 0 to 70;
(ii") contacting the mixture obtained in step (I") comprising (A) one or more crosslinked hyaluronic acids of formula (I) and formula (II) and (B) one or more polyglycerols of formula (III) or formula (IV) with the one or more anesthetic agents (C);
(iii") optionally, contacting the mixture obtained in step (ii") with the one or more excipients or carriers (D); and
(iv") optionally, sterilizing the mixture obtained in step (iii").

Clause 11. The composition according to clause 10, wherein:
when the composition comprises (a) a crosslinked hyaluronic acid of formula (I), the composition is obtainable by a process which comprises:
i) crosslinking a hyaluronic acid with a compound of formula (V) having:
a molecular weight ($M_w$) from 204 to 15.000 Da measured by the method by size exclusion chromatography (SEC); and
an epoxy equivalent weight from 100 to 7.000 g/eq measured by ultrasonication-assisted rapid titration with HCl;
or alternatively,
when the composition comprises (a) a crosslinked hyaluronic acid of formula (II), then the composition is obtainable by a process which comprises:
i') crosslinking a hyaluronic acid with a compound of formula (VI) having:
a molecular weight ($M_w$) from 204 to 15.000 Da measured by the method by size exclusion chromatography (SEC); and
an epoxy equivalent weight from 100 to 7.000 g/eq measured by ultrasonication-assisted rapid titration with HCl;
or alternatively,
when the composition comprises (a) a mixture of a crosslinked hyaluronic acid of formula (I) and of formula (II); then the composition is obtainable by a process which comprises:
I") crosslinking a hyaluronic acid with a mixture comprising the compound of formula (V) and the compound of formula (VI) having:
a molecular weight ($M_w$) from 204 to 15.000 Da measured by the method by size exclusion chromatography (SEC); and
an epoxy equivalent weight from 100 to 7.000 g/eq measured by ultrasonication-assisted rapid titration with HCl.

Clause 12. the composition according to any of the clauses 10 or 11, wherein:
when the composition comprises (a) a crosslinked hyaluronic acid of formula (I), then the composition is obtainable by a process which comprises an additional step (v) after step (ii); or alternatively after step (iii), or alternatively after step (iv) comprising the addition of a compound of formula (III), a compound of formula (IV) or a mixture thereof;
or alternatively,
when the composition comprises (a) a crosslinked hyaluronic acid of formula (II), then the composition is obtainable by a process which comprises an additional step (v') after step (ii'); or alternatively after step (iii'), or alternatively after step (iv') comprising the addition of a compound of formula (III), a compound of formula (IV) or a mixture thereof;

or alternatively, when the composition comprises (a) a mixture of a crosslinked hyaluronic acid of formula (I) and of formula (II); then the composition is obtainable by a process which comprises an additional step (v") after step (ii"); or alternatively after step (iii"), or alternatively after step (iv") comprising the addition of a compound of formula (III), a compound of formula (IV) or a mixture thereof.

Clause 13. The composition according to any of the clauses 1-12, which is in form of injectable composition.

Clause 14 The composition as defined in any of the clauses 1-13, which is a pharmaceutical composition comprising:
- a therapeutically effective amount of the one or more crosslinked hyaluronic acids of formula (I), of formula (II) or a mixture thereof;
- a therapeutically effective amount of the one or more polyglycerols of formula (III) or formula (IV) or a mixture thereof;
- a therapeutically effective amount of one or more anesthetic agents, and
- optionally, one or more pharmaceutically acceptable excipients or carriers; for use in therapy;

or alternatively, the use of a composition as defined in any of the clauses 1-13, which is a cosmetic composition comprising:
- a cosmetically effective amount of the one or more crosslinked hyaluronic acids of formula (I), of formula (II) or a mixture thereof;
- a cosmetically effective amount of the one or more polyglycerols of formula (III) or formula (IV) or a mixture thereof;
- a cosmetically effective amount of one or more anesthetic agents, and
- optionally, one or more cosmetically acceptable excipients or carriers, as skin care agent; particularly as dermal filler.

Clause 15. Use of a composition according to any of the clauses 1-13, as a carrier; particularly as a drug delivery system.

The invention claimed is:

1. A composition comprising:
A) one or more crosslinked hyaluronic acids selected from the group consisting of one or more crosslinked hyaluronic acids of formula (I);

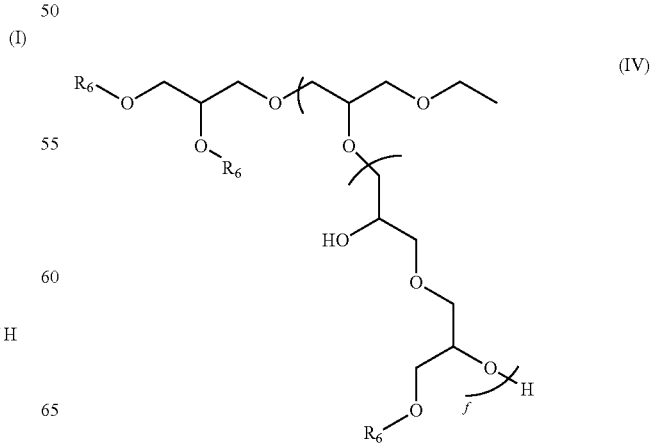

(I)

one or more crosslinked hyaluronic acids of formula (II);

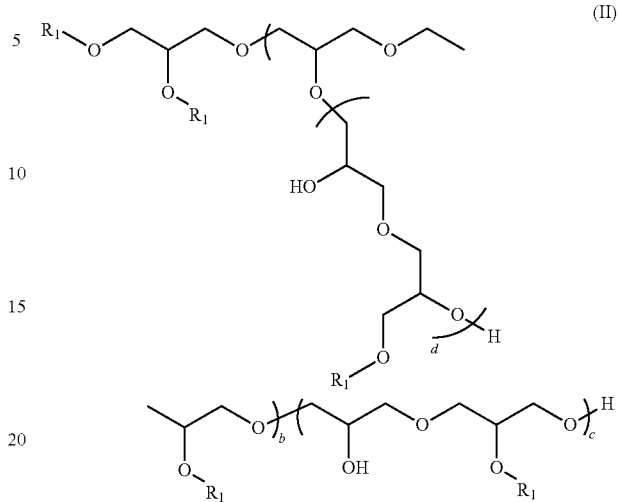

(II)

and a mixture of one or more crosslinked hyaluronic acids of formula (I) and one or more crosslinked hyaluronic acids of formula (II);

B) one or more polyglycerols selected from the group consisting of one or more polyglycerols of formula (III);

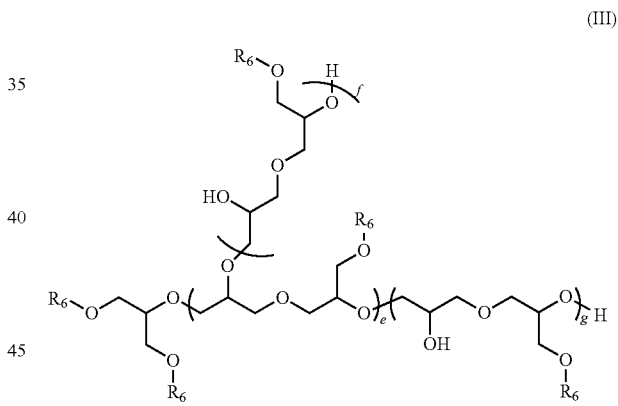

(III)

one or more polyglycerols of formula (IV);

(IV)

-continued

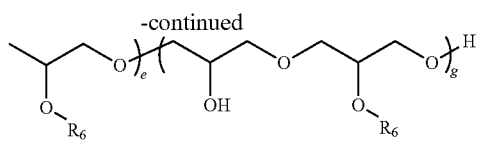

and a mixture of one or more polyglycerols of formula (III) and one or more polyglycerols of formula (IV);

C) one or more local anesthetic agents or a salt thereof; and

D) optionally, one or more acceptable excipients or carriers;

wherein:

each $R_1$ is independently selected from the group consisting of $R_2$, $R_4$ and $R_5$;

$R_2$

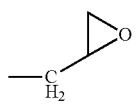

$R_4$ is

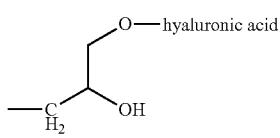

$R_5$ is

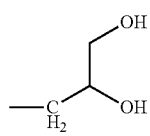

each $R_6$ is $R_5$;

b is an integer selected from the group consisting of 1 to 70;

c is an integer selected from the group consisting of 0 to 70;

d is an integer selected from the group consisting of 0 to 70;

e is an integer selected from the group consisting of 1 to 50;

f is an integer selected from the group consisting of 0 to 50;

g is an integer selected from the group consisting of 0 to 50;

the crosslinked hyaluronic acids of formula (I) or formula (II) have a crosslinking percentage (C.D.) from 0.030% to 0.900%;

the polyglycerols of formula (III) or formula (IV) have a weight average molecular weight ($M_w$) from 240 to 3700 Da measured by size exclusion chromatography coupled with UV-visible and Mass detector (SEC/UV/MS); and the concentration of polyglycerols of formula (III) or formula (IV) or mixture thereof in the composition is from 0.45 to 25 mg/mL;

with the proviso that:

in the crosslinked hyaluronic acids of formula (I) or formula (II) at least two $R_1$ are $R_4$;

wherein:

the composition comprises (a) a crosslinked hyaluronic acid of formula (I) and is obtained by a process which comprises:

(i) crosslinking a hyaluronic acid with a compound of formula (V)

(V)

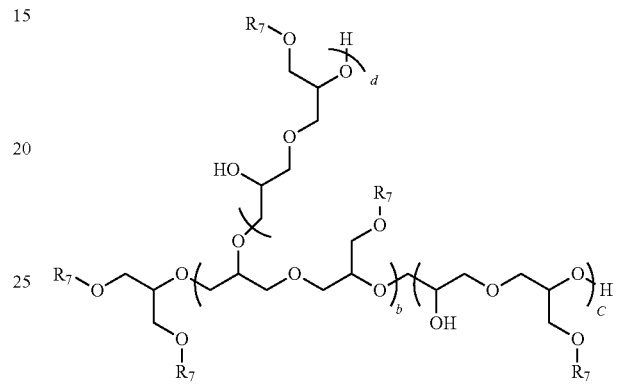

wherein:

each $R_7$ is $R_2$;

$R_2$ is

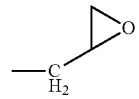

b is an integer selected from the group consisting of 1 to 70;

c is an integer selected from the group consisting of 0 to 70;

d is an integer selected from the group consisting of 0 to 70;

(ii) contacting the mixture obtained in step (i) comprising (A) one or more crosslinked hyaluronic acids of formula (I) and (B) one or more polyglycerols of formula (III) or formula (IV) with the one or more anesthetic agents (C);

(iii) optionally, contacting the mixture obtained in step (ii) with the one or more excipients or carriers (D); and (iv) optionally, sterilizing the mixture obtained in step (iii);

wherein the process further comprises an additional washing step (vi) after step (i);

or alternatively, the composition comprises (a) a crosslinked hyaluronic acid of formula (II) and is obtained by a process which comprises:

(i') crosslinking a hyaluronic acid with a compound of formula (VI)

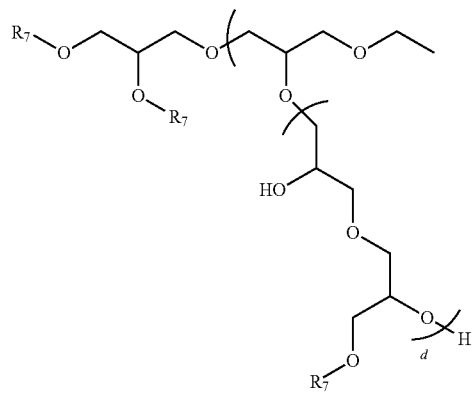

(VI)

wherein:
each $R_7$ is $R_2$;
$R_2$ is

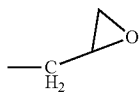

b is an integer selected from the group consisting of 1 to 70;
c is an integer selected from the group consisting of 0 to 70;
d is an integer selected from the group consisting of 0 to 70;

(ii') contacting the mixture obtained in step (i') comprising (A) one or more crosslinked hyaluronic acids of formula (II) and (B) one or more polyglycerols of formula (III) or formula (IV) with the one or more anesthetic agents (C);

(iii') optionally, contacting the mixture obtained in step (ii') with the one or more excipients or carriers (D); and (iv') optionally, sterilizing the mixture obtained in step (iii');

wherein the process further comprises an additional washing step (vi') after step (i');

or alternatively, the composition comprises (a) a mixture of a crosslinked hyaluronic acid of formula (I) and of formula (II) and the composition is obtained by a process which comprises:

(i'') crosslinking a hyaluronic acid with a mixture comprising the compound of formula (V)

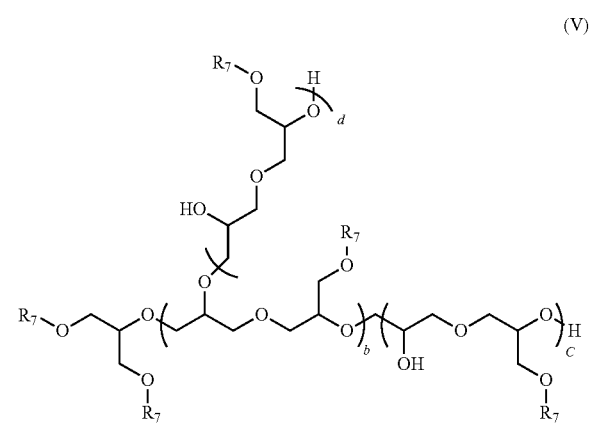

(V)

and of formula (VI)

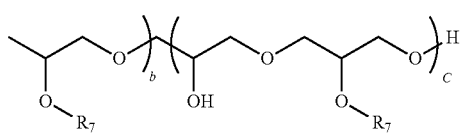

(VI)

wherein:
each $R_7$ is $R_2$;
$R_2$ is

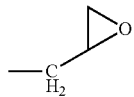

b is an integer selected from the group consisting of 1 to 70;
c is an integer selected from the group consisting of 0 to 70;
d is an integer selected from the group consisting of 0 to 70;
(ii") contacting the mixture obtained in step (i") comprising (A) one or more crosslinked hyaluronic acids of formula (I) and formula (II) and (B) one or more polyglycerols of formula (III) or formula (IV) with the one or more anesthetic agents (C);
(iii") optionally, contacting the mixture obtained in step (ii") with the one or more excipients or carriers (D); and
(iv") optionally, sterilizing the mixture obtained in step (iii");
wherein the process further comprises an additional washing step (vi") after step (ii");
wherein step (vi), or alternatively step (vi'), or alternatively step (vi") is performed by the addition of
such appropriate amount of an acidic water solution to obtain a pH from 6.5-7.4 and a concentration of polyglycerols of formula (III) or formula (IV) or mixture thereof in the composition from 0.45 to 25 mg/mL.

2. The composition according to claim 1, wherein the crosslinked hyaluronic acid of formula (I), or of formula (II), or a mixture thereof, is obtained using polyglycerol polyglycidyl ether (PPE) as crosslinker having a weight average molecular weight from 204 to 15000 Da measured by the method by size exclusion chromatography (SEC) and an epoxy equivalent weight from 100 to 7000 g/eq measured by ultrasonication-assisted rapid titration with HCl.

3. The composition according to claim 1, wherein the one or more polyglycerols of formula (III) or formula (IV) is selected from the group consisting of:
a compound of formula (4);

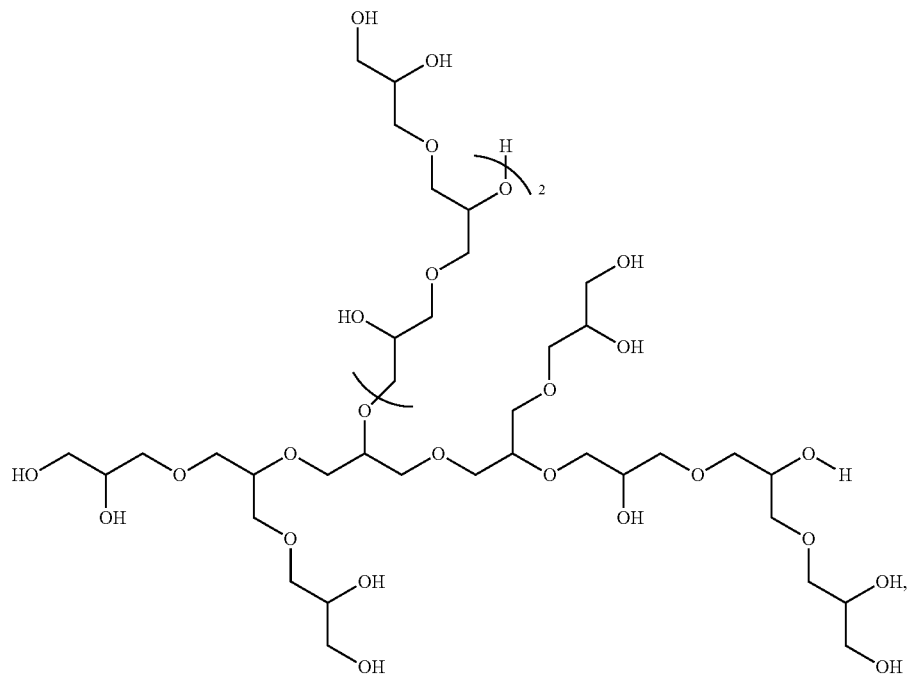

a compound of formula (5);

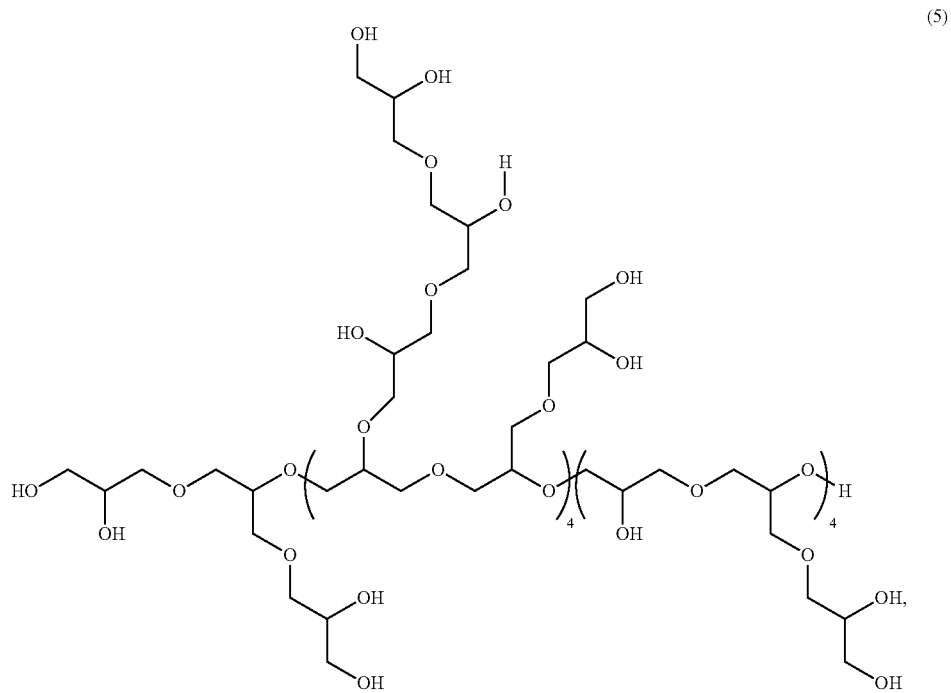

and a mixture thereof.

4. The composition according to claim 1, wherein the concentration of the hyaluronic acid in the crosslinked hyaluronic acid of formula (I) or formula (II) is from 1 to 50 mg/ml.

5. The composition according to claim 1, wherein the weight average molecular weight of the hyaluronic acid of the crosslinked hyaluronic acid of formula (I) or formula (II) is from 100 to 3000 kDa measured by the method by size exclusion chromatography (SEC).

6. The composition according to claim 1, wherein the local anesthetic agent is selected from the group consisting of ambucaine, amolanone, amylocaine, articaine, benoxinate, benzocaine, betoxycaine, biphenamine, bupivacaine, butacaine, butamben, butanilicaine, butethamine, butoxycaine, chloroprocaine, cocaethylene, cocaine, cyclomethycaine, dibucaine, dimethyisoquin, dimethocaine, diperodon, dicyclomine, ecgonidine, ecgonine, etidocaine, beta-eucaine, euprocin, fenalcomine, farmocaine, fomocaine, hexylcaine, hydroxytetracaine, isobutyl p-aminobenzoate, leucinocaine mesylate, levoxadrol, lidocaine, mepivacaine, meprylcaine, metabutoxycaine, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and a mixture thereof.

7. The composition according to claim 1, wherein:
the composition comprises (a) a crosslinked hyaluronic acid of formula (I) and is obtained by a process which comprises:
(i) crosslinking a hyaluronic acid with a compound of formula (V) having:
a weight average molecular weight ($M_w$) from 204 to 15000 Da measured by the method by size exclusion chromatography (SEC); and
an epoxy equivalent weight from 100 to 7000 g/eq measured by ultrasonication-assisted rapid titration with HCl;
or alternatively,
the composition comprises (a) a crosslinked hyaluronic acid of formula (II) and is obtained by a process which comprises:
(i') crosslinking a hyaluronic acid with a compound of formula (VI) having:
a weight average molecular weight ($M_w$) from 204 to 15000 Da measured by the method by size exclusion chromatography (SEC); and
an epoxy equivalent weight from 100 to 7000 g/eq measured by ultrasonication-assisted rapid titration with HCl;
or alternatively,
the composition comprises (a) a mixture of a crosslinked hyaluronic acid of formula (I) and of formula (II) and is obtained by a process which comprises:
(i") crosslinking a hyaluronic acid with a mixture comprising the compound of formula (V) and the compound of formula (VI) having:
a weight average molecular weight ($M_w$) from 204 to 15000 Da measured by the method by size exclusion chromatography (SEC); and
an epoxy equivalent weight from 100 to 7000 g/eq measured by ultrasonication-assisted rapid titration with HCl.

8. The composition according to claim 1 wherein:
the composition comprises (a) a crosslinked hyaluronic acid of formula (I) and is obtained by a process which comprises an additional step (v) after step (ii); or alternatively after step (iii), or alternatively after step (iv) comprising the addition of a compound of formula (III), a compound of formula (IV) or a mixture thereof;

or alternatively, the composition comprises (a) a crosslinked hyaluronic acid of formula (II) and the composition is obtained by a process which comprises an additional step (v') after step (ii'); or alternatively after step (iii'), or alternatively after step (iv') comprising the addition of a compound of formula (III), a compound of formula (IV) or a mixture thereof;

or alternatively, the composition comprises (a) a mixture of a crosslinked hyaluronic acid of formula (I) and of formula (II) and the composition is obtained by a process which comprises an additional step (v") after step (ii"); or alternatively after step (iii"), or alternatively after step (iv") comprising the addition of a compound of formula (III), a compound of formula (IV) or a mixture thereof.

9. The composition according to claim 1, which is in form of injectable composition.

* * * * *